(12) United States Patent
Bouffier

(10) Patent No.: US 12,302,852 B2
(45) Date of Patent: May 20, 2025

(54) HYBRID PEPPER PLANT NAMED ALTATA

(71) Applicant: HM.CLAUSE, Inc., Davis, CA (US)

(72) Inventor: Bruno Bouffier, Naples, FL (US)

(73) Assignee: HM.CLAUSE, INC., Davis, CA (US)

( * ) Notice: Subject to any disclaimer, the term of this patent is extended or adjusted under 35 U.S.C. 154(b) by 319 days.

(21) Appl. No.: 17/871,704

(22) Filed: Jul. 22, 2022

(65) Prior Publication Data

US 2024/0023508 A1    Jan. 25, 2024

(51) Int. Cl.
- *A01H 5/08* (2018.01)
- *A01H 1/00* (2006.01)
- *A01H 6/82* (2018.01)

(52) U.S. Cl.
CPC ............... *A01H 6/822* (2018.05); *A01H 1/00* (2013.01); *A01H 5/08* (2013.01)

(58) Field of Classification Search
None
See application file for complete search history.

(56) References Cited

U.S. PATENT DOCUMENTS

| | | | |
|---|---|---|---|
| 10,143,175 B2 | 12/2018 | Monroy | |
| 10,420,315 B2 | 9/2019 | Monroy | |
| 10,420,316 B2 | 9/2019 | Monroy | |
| 10,517,262 B2 | 12/2019 | Monroy | |
| 10,561,113 B2 | 2/2020 | Monroy | |
| 10,568,295 B2 | 2/2020 | Denet | |
| 10,575,494 B2 | 3/2020 | Denet | |
| 11,324,174 B2 | 5/2022 | Noguera Diaz | |
| 11,388,870 B2 | 7/2022 | Denet | |
| 2017/0055478 A1* | 3/2017 | Milligan | A01H 5/08 |
| 2018/0077886 A1 | 3/2018 | Monroy | |
| 2018/0077887 A1 | 3/2018 | Monroy | |
| 2018/0077888 A1 | 3/2018 | Monroy | |
| 2019/0327925 A1 | 10/2019 | Monroy | |
| 2019/0327926 A1 | 10/2019 | Monroy | |
| 2019/0335700 A1 | 11/2019 | Denet | |
| 2019/0335701 A1 | 11/2019 | Denet | |
| 2021/0059143 A1 | 3/2021 | Denet | |
| 2021/0059144 A1 | 3/2021 | Denet | |

OTHER PUBLICATIONS

Larkin et al., Theor. Appl. Genet., vol. 60, 1981, pp. 197-214.*
Allard, 1960. Principle of Plant Breeding. John Wiley & Sons, Inc. p. 55.
Darnell, et al., 1990. DNA Replication, Repair and Recombination. In Molecular Cell Biology, 2nd edition, W.H. Freeman and Co., p. 478-487.
Poehlman, J.M. and Sleeper, D.A., Methods in Plant Breeding. In Breeding Field Crops, 5th ed. (2006), Iowa State University Press, pp. 171-183.

* cited by examiner

*Primary Examiner* — Phuong T Bui
(74) *Attorney, Agent, or Firm* — McKee, Voorhees & Sease, PLC

(57) ABSTRACT

A hybrid pepper plant designated ALTATA is disclosed. The disclosure relates to the seeds of pepper hybrid ALTATA, to the plants and plant parts of hybrid pepper ALTATA, and to methods for producing a pepper plant by crossing the hybrid pepper ALTATA with itself or another pepper plant.

25 Claims, No Drawings

HYBRID PEPPER PLANT NAMED ALTATA

FIELD OF THE INVENTION

The present invention relates to the field of agriculture, to new and distinctive hybrid pepper plants, such as hybrid plant designated ALTATA and to methods of making and using such hybrids.

BACKGROUND OF THE INVENTION

The following description includes information that may be useful in understanding the present invention. It is not an admission that any of the information provided herein is prior art or relevant to the presently claimed inventions, or that any publication specifically or implicitly referenced is prior art.

Pepper is an important and valuable vegetable crop. Thus, a continuing goal of plant breeders is to develop stable, high yielding pepper hybrids that are agronomically sound or unique. The reasons for this goal are to maximize the amount of fruit produced on the land used (yield) as well as to improve the fruit appearance, the fruit shape and size, eating and processing qualities and/or the plant agronomic and horticultural qualities. To accomplish this goal, the pepper breeder must select and develop pepper plants that have the traits that result in superior parental lines that combine to produce superior hybrids.

SUMMARY OF THE INVENTION

The following embodiments and aspects thereof are described in conjunction with systems, tools and methods which are meant to be exemplary, not limiting in scope.

In various embodiments, one or more of the above-described problems have been reduced or eliminated, while other embodiments are directed to other improvements.

According to the invention, in some embodiments there is provided a novel hybrid pepper, designated ALTATA.

This invention thus relates to the seeds of hybrid pepper designated ALTATA, to the plants or parts thereof of hybrid pepper designated ALTATA, to plants or parts thereof consisting essentially all of the physiological and morphological characteristics of hybrid pepper designated ALTATA or parts thereof, and/or having all the physiological and morphological characteristics of hybrid pepper designated ALTATA, and/or having one or more or all of the characteristics of hybrid pepper designated ALTATA listed in Table 1 including but not limited to as determined at the 5% significance level when grown in the same environmental conditions, and/or having one or more of the physiological and morphological characteristics of hybrid pepper designated ALTATA listed in Table 1 including but not limited to as determined at the 5% significance level when grown in the same environmental conditions and/or having all the physiological and morphological characteristics of hybrid pepper designated ALTATA listed in Table 1 including but not limited to as determined at the 5% significance level when grown in the same environmental conditions and/or having all the physiological and morphological characteristics of hybrid pepper designated ALTATA listed in Table 1 when grown in the same environmental conditions. The invention also relates to variants, mutants and trivial modifications of the seed or plant of hybrid pepper designated ALTATA.

Plant parts of the hybrid pepper plant of the present invention are also provided, such as, but not limited to, a scion, a rootstock, a fruit, leaf, flower, peduncle, stalk, root, anther cell, pollen or ovule obtained from the hybrid plant. The present invention provides fruit of the hybrid pepper of the present invention. Such fruit and parts thereof could be used as fresh products for consumption or in processes resulting in processed products such as food products comprising one or more harvested part of the hybrid pepper designated ALTATA, such as prepared fruit or parts thereof, canned fruit or parts thereof, freeze dried or frozen fruit or parts thereof, diced fruits, juice, prepared fruit cuts, canned pepper, pastes, sauces, puree and the like. All such products are part of the present invention and the like. The harvested part or food product can be or can comprise hybrid pepper fruit from hybrid pepper designated ALTATA. The food products might have undergone one or more processing steps such as, but not limited to cutting, washing, mixing, frizzing, canning, etc. All such products are part of the present invention. The present invention also provides plant parts or cells, wherein a plant regenerated from said plants parts or cells has one or more, or essentially all of the phenotypic and morphological characteristics of hybrid pepper designated ALTATA, such as one or more or all of the characteristics of hybrid pepper designated ALTATA, listed in Table 1 including but not limited to as determined at the 5% significance level when grown in the same environmental conditions.

The plants and seeds of the present invention include those that may be of an essentially derived variety as defined in section 41(3) of the Plant Variety Protection Act of The United States of America, e.g., a variety that is predominantly derived from hybrid pepper designated ALTATA or from a variety that i) is predominantly derived from hybrid pepper designated ALTATA, while retaining the expression of the essential characteristics that result from the genotype or combination of genotypes of hybrid pepper designated ALTATA; ii) is clearly distinguishable from hybrid pepper designated ALTATA; and iii) except for differences that result from the act of derivation, conforms to the initial variety in the expression of the essential characteristics that result from the genotype or combination of genotypes of the initial variety.

In another aspect, the present invention provides regenerable cells. In some embodiments, the regenerable cells are for use in tissue culture of hybrid pepper designated ALTATA. In some embodiments, the tissue culture is capable of regenerating plants consisting essentially all of the physiological and morphological characteristics of hybrid pepper designated ALTATA, and/or having all the physiological and morphological characteristics of hybrid pepper designated ALTATA, and/or having the physiological and morphological characteristics of hybrid pepper designated ALTATA, and/or having the characteristics of hybrid pepper designated ALTATA. In one embodiment, the regenerated plants have the characteristics of hybrid pepper designated ALTATA listed in Table 1 including but not limited to as determined at the 5% significance level when grown in the same environmental conditions.

In some embodiments, the plant parts and cells used to produce such tissue cultures will be embryos, meristematic cells, seeds, callus, pollen, leaves, anthers, pistils, roots, root tips, stems, petioles, fruits, cotyledons, hypocotyls, ovaries, seed coat, fruits, stalks, endosperm, flowers, axillary buds or the like. Protoplasts produced from such tissue culture are also included in the present invention. The pepper shoots, roots and whole plants regenerated from the tissue culture, as well as the fruit produced by said regenerated plants are also part of the invention. In some embodiments, the whole plants regenerated from the tissue culture have one, more than one, or all of the physiological and morphological characteristics of pepper hybrid designated ALTATA listed in Table 1 including but not limited to as determined at the 5% significance level when grown in the same environmental conditions.

The invention also discloses methods for vegetatively propagating a plant of the present invention. In the present application, vegetatively propagating can be interchangeably used with vegetative reproduction. In some embodiments, the methods comprise collecting a part of a hybrid pepper designated ALTATA and regenerating a plant from said part. In some embodiments, the part can be for example a stem cutting that is rooted into an appropriate medium according to techniques known by the one skilled in the art. Plants, plant parts and fruits thereof produced by such methods are also included in the present invention. In another aspect, the plants and fruits thereof produced by such methods consist essentially all of the physiological and morphological characteristics of hybrid pepper designated ALTATA, and/or having all the physiological and morphological characteristics of hybrid pepper designated ALTATA and/or having the physiological and morphological characteristics of hybrid pepper designated ALTATA and/or having the characteristics of hybrid pepper designated ALTATA. In some embodiments, plants or fruits thereof produced by such methods consist of one, more than one, or all physiological and morphological characteristics of pepper hybrid designated ALTATA listed in Table 1 including but not limited to as determined at the 5% significance level when grown in the same environmental conditions.

Further included in the invention are methods for producing fruits and/or seeds from the hybrid pepper designated ALTATA. In some embodiments, the methods comprise growing a hybrid pepper designated ALTATA to produce pepper fruits and/or seeds. In some embodiments, the methods further comprise harvesting the hybrid pepper fruits and/or seeds. Such fruits and/or seeds are part of the present invention. In some embodiments, such fruits and/or seeds have all the physiological and morphological characteristics of fruit and seed of hybrid pepper designated ALTATA (e.g. those listed in Table 1) when grown in the same environmental conditions.

Also included in this invention are methods for producing a pepper plant. In some embodiments, the pepper plant is produced by crossing the hybrid pepper designated ALTATA with itself or another pepper plant. In some embodiments, the other plant can be a pepper hybrid or line. When crossed with an inbred line, in some embodiments, a "three-way cross" is produced. When crossed with itself or with another, different hybrid pepper, in some embodiments, a "four-way" cross is produced. Such three and four-way hybrid seeds and plants produced by growing said three and four-way hybrid seeds are included in the present invention. Methods for producing a three and four-way hybrid pepper seed comprising crossing hybrid pepper designated ALTATA pepper plant with a different pepper line or hybrid and harvesting the resultant hybrid pepper seed are also part of the invention. The hybrid pepper seeds produced by the method comprising crossing hybrid pepper designated ALTATA pepper plant with a different pepper plant and harvesting the resultant hybrid pepper seed are included in the invention, as are included the hybrid pepper plant or parts thereof and seeds produced by said grown hybrid pepper plants.

Further included in the invention are methods for producing pepper seeds and plants made thereof. In some embodiments, the methods comprise self-pollinating the hybrid pepper designated ALTATA and harvesting the resultant hybrid seeds. Pepper seeds produced by such method are also part of the invention.

In another embodiment, this invention relates to methods for producing a hybrid pepper designated ALTATA from a collection of seeds. In some embodiments, the collection contains both seeds of inbred parent line(s) of hybrid pepper designated ALTATA seeds and hybrid seeds of ALTATA. Such a collection of seeds might be a commercial bag of seeds. In some embodiments, said methods comprise planting the collection of seeds. When planted, the collection of seeds will produce inbred parent lines of hybrid pepper ALTATA and hybrid plants from the hybrid seeds of ALTATA. In some embodiments, said inbred parent lines of hybrid pepper designated ALTATA plants are identified as having a decreased vigor compared to the other plants (i.e. hybrid plants) grown from the collection of seeds. In some embodiments, said decreased vigor is due to the inbreeding depression effect and can be identified for example by a less vigorous appearance for vegetative and/or reproductive characteristics including a shorter plant height, small fruit size, fruit shape, fruit color or other characteristics. In some embodiments, seeds of the inbred parent lines of the hybrid pepper ALTATA are collected and, if new inbred plants thereof are grown and crossed in a controlled manner with each other, the hybrid pepper ALTATA will be recreated.

This invention also relates to methods for producing other pepper plants derived from hybrid pepper ALTATA and to the pepper plants derived by the use of those methods.

In some embodiments, such methods for producing a pepper plant derived from the hybrid variety ALTATA comprise (a) self-pollinating the hybrid pepper ALTATA plant at least once to produce a progeny plant derived from pepper hybrid ALTATA; In some embodiments, the methods further comprise (b) crossing the progeny plant derived from pepper hybrid ALTATA with itself or a second pepper plant to produce a seed of a progeny plant of a subsequent generation; In some embodiments, the methods further comprise (c) growing the progeny plant of the subsequent generation; In some embodiments, the methods further comprise (d) crossing the progeny plant of the subsequent generation with itself or a second pepper plant to produce a pepper plant further derived from the hybrid pepper ALTATA. In further embodiments, steps (b), (c) and/or (d) are repeated for at least 1, 2, 3, 4, 5, 6, 7, 8, or more generations to produce a pepper plant derived from the hybrid pepper variety ALTATA. In some embodiments, within each crossing cycle, the second plant is the same plant as the second plant in the last crossing cycle. In some embodiments, within each crossing cycle, the second plant is different from the second plant in the last crossing cycle.

Another method for producing a pepper plant derived from the hybrid variety ALTATA, comprises the steps of: (a) crossing the hybrid pepper ALTATA plant with a second pepper plant to produce a progeny plant derived from pepper hybrid ALTATA; In some embodiments, the method further comprise (b) crossing the progeny plant derived from pepper hybrid ALTATA with itself or a second pepper plant to produce a seed of a progeny plant of a subsequent generation; In some embodiments, the method further comprise (c) growing the progeny plant of the subsequent generation; In some embodiments, the method further comprise (d) crossing the progeny plant of the subsequent generation with itself or a second pepper plant to produce a pepper plant derived from the hybrid pepper variety ALTATA. In a further embodiment, steps (b), (c) and/or (d) are repeated for at least 1, 2, 3, 4, 5, 6, 7, 8, or more generations to produce a pepper plant derived from the hybrid pepper variety ALTATA. In some embodiments, within each crossing cycle, the second plant is the same plant as the second plant in the last crossing cycle. In some embodiments, within each crossing cycle, the second plant is different from the second plant in the last crossing cycle.

In another aspect, the present invention provides methods of introducing or modifying one or more desired trait(s) into the hybrid pepper ALTATA and plants or seeds obtained from such methods. The desired trait(s) may be, but not exclusively, a single gene. In some embodiments, the gene is a dominant allele. In some embodiments, the gene is a partially dominant allele. In some embodiments, the gene is a recessive allele. In some embodiments, the gene or genes will confer such traits, including but not limited to male sterility, herbicide resistance, insect resistance, resistance for bacterial, fungal, mycoplasma or viral disease, enhanced plant quality such as improved drought or salt tolerance, water-stress tolerance, improved standability, enhanced plant vigor, improved shelf life, delayed senescence or controlled ripening, enhanced nutritional quality such as increased sugar content or increased sweetness, increased texture, flavor and aroma, improved fruit length and/or size, protection for color, fruit shape, uniformity, length or diameter, refinement or depth, lodging resistance, yield and recovery, improve fresh cut application, specific aromatic compounds, specific volatiles, flesh texture, specific nutritional components. For the present invention and the skilled artisan, disease is understood to include, but not limited to fungal diseases, viral diseases, bacterial diseases, mycoplasm diseases, or other plant pathogenic diseases and a disease resistant plant will encompass a plant resistant to fungal, viral, bacterial, mycoplasm, and other plant pathogens. The gene or genes may be naturally occurring pepper gene(s), mutant(s), or genes modified through the use of New Breeding Techniques. In some embodiments, the method for introducing the desired trait(s) is a backcrossing process making use of a series of backcrosses to at least one of the parent lines of hybrid pepper ALTATA during which the desired trait(s) is maintained by selection. The single gene conversion plants that can be obtained by the methods are included in the present invention.

When dealing with a gene that has been modified, for example through New Breeding Techniques, the trait (genetic modification) could be directly modified into the newly developed line/cultivar such as at least one of the parent lines of hybrid pepper ALTATA. Alternatively, if the trait is not modified into each newly developed line/cultivar such as at least one of the parent lines of hybrid pepper ALTATA, another typical method used by breeders of ordinary skill in the art to incorporate the modified gene is to take a line already carrying the modified gene and to use such line as a donor line to transfer the modified gene into one or more of the parents of the newly developed hybrid.

The same would apply for a naturally occurring trait or one arising from spontaneous or induced mutations.

In some embodiments, the backcross breeding process of hybrid pepper ALTATA comprises (a) crossing one of the parental inbred line plants of ALTATA with plants of another line that comprise the desired trait(s) to produce F1 progeny plants In some embodiments, the process further comprises (b) selecting the F1 progeny plants that have the desired trait(s) In some embodiments, the process further comprises (c) crossing the selected F1 progeny plants with the parental inbred pepper lines of hybrid ALTATA plants to produce backcross progeny plants In some embodiments, the process further comprises (d) selecting for backcross progeny plants that have the desired trait(s) and physiological and morphological characteristics of the pepper parental inbred line of hybrid pepper ALTATA to produce selected backcross progeny plants; In some embodiments, the process further comprises (e) repeating steps (c) and (d) one, two, three, four, five six, seven, eight, nine or more times in succession to produce selected, second, third, fourth, fifth, sixth, seventh, eighth, ninth or higher backcross progeny plants that have the desired trait(s) and otherwise consist essentially all of the physiological and morphological characteristics of the parental inbred pepper line of hybrid pepper ALTATA, and/or have the desired trait(s) and otherwise the physiological and morphological characteristics of the parental pepper inbred line of hybrid pepper ALTATA, and/or have all the desired trait(s) and otherwise the physiological and morphological characteristics of the parental inbred pepper line of pepper hybrid ALTATA as determined in Table 1, including but not limited to when grown in the same environmental conditions or including but not limited to at a 5% significance level when grown in the same environmental conditions. The pepper plants or seed produced by the methods are also part of the invention, as are the hybrid pepper ALTATA plants that comprised the desired trait. Backcrossing breeding methods, well known to one skilled in the art of plant breeding will be further developed in subsequent parts of the specification.

In an embodiment of this invention is a method of making a backcross conversion of hybrid pepper ALTATA. In some embodiments, the method comprises crossing one of the parental pepper inbred line plants of hybrid ALTATA with a donor plant comprising a mutant gene(s), a naturally occurring gene(s) or a gene(s) and/or sequences modified through New Breeding Techniques conferring one or more desired trait to produce F1 progeny plants. In some embodiments, the method further comprises selecting an F1 progeny plant comprising the naturally occurring gene(s), mutant gene(s) or modified gene(s) and/or sequences conferring the one or more desired trait; In some embodiments, the method further comprises backcrossing the selected progeny plant to the parental pepper inbred line plants of hybrid ALTATA. This method may further comprise the step of obtaining a molecular marker profile of the parental pepper inbred line plants of hybrid ALTATA and using the molecular marker profile to select for the progeny plant with the desired trait and the molecular marker profile of the parental pepper inbred line plants of hybrid ALTATA. In some embodiments, this method further comprises crossing the backcross progeny plant ALTATA containing the naturally occurring gene (s), the mutant gene(s) or the modified gene(s) and or sequences conferring the one or more desired trait with the second parental inbred pepper line plants of hybrid pepper ALTATA in order to produce the hybrid pepper ALTATA comprising the naturally occurring gene(s), the mutant gene (s) or modified gene(s) and/or sequences conferring the one or more desired traits. The plants or parts thereof produced by such methods are also part of the present invention.

In some embodiments of the invention, the number of loci that may be backcrossed into the parental pepper inbred line of hybrid ALTATA is at least 1, 2, 3, 4, 5, or more.

A single locus may contain several genes. A single locus conversion also allows for making one or more site specific changes to the plant genome, such as, without limitation, one or more nucleotide change, deletion, insertions, etc. In some embodiments, the single locus conversion is performed by genome editing, a.k.a. genome editing with engineered nucleases (GEEN). In some embodiments, the genome editing comprises using one or more engineered nucleases. In some embodiments, the engineered nucleases include, but are not limited to Zinc finger nucleases (ZFNs), Transcription Activator-Like Effector Nucleases (TALENs), the CRISPR/Cas system, and engineered meganuclease re-engineered homing endonucleases and endonucleases for DNA guided genome editing (Gao et al., Nature Biotechnology (2016), doi: 10.1038/nbt.3547). In some embodiments, the single locus conversion changes one or several nucleotides of the plant genome. Such genome editing techniques are some of the techniques now known by the person skilled in the art and herein are collectively referred to as "New Breeding Techniques". In some embodiments, one or more above-mentioned genome editing method is directly applied on a plant of the present invention, rather than the parental pepper inbred lines of hybrid ALTATA. Accordingly, a cell containing edited genome, or a plant part containing such cell can be isolated and used to regenerate a novel plant which has a new trait conferred by said genome editing, and otherwise all of the physiological and morphological characteristics of hybrid pepper plant ALTATA.

The invention further provides methods for developing pepper plants in a pepper plant breeding program using plant breeding techniques including but not limited to, recurrent selection, backcrossing, pedigree breeding, genomic selection, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites, Single Nucleotide Polymorphism (SNP), etc.) enhanced selection, genetic marker enhanced selection and transformation. Seeds, pepper plants, and parts thereof produced by such breeding methods are also part of the invention.

The invention also relates to variants, mutants and trivial modifications of the seed or plant of the pepper hybrid ALTATA or inbred parental lines thereof. Variants, mutants and trivial modifications of the seed or plant of hybrid pepper ALTATA or inbred parental lines thereof can be generated by methods available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knockouts/knock-ins, antisense and RNA interference and other techniques such as the New Breeding Techniques. For more information of mutagenesis in plants, such as agents or protocols, see Acquaah et al. (Principles of plant genetics and breeding, Wiley-Blackwell, 2007, ISBN 1405136464, 9781405136464, which is herein incorporated by reference in its entity).

The invention also relates to a mutagenized population of the hybrid pepper ALTATA and methods of using such populations. In some embodiments, the mutagenized population can be used in screening for new pepper plants which comprise one or more or all of the morphological and physiological characteristics of hybrid pepper ALTATA. In some embodiments, the new pepper plants obtained from the screening process comprise all of the morphological and physiological characteristics of the pepper hybrid ALTATA and one or more additional or different morphological and physiological characteristics that the pepper hybrid ALTATA does not have.

This invention also is directed to methods for producing a pepper plant by crossing a first parent pepper plant with a second parent pepper plant wherein either the first or second parent pepper plant is a hybrid pepper plant of ALTATA. Further, both first and second parent pepper plants can come from the hybrid pepper plant ALTATA. Further, the hybrid pepper plant ALTATA can be self-pollinated i.e. the pollen of a hybrid pepper plant ALTATA can pollinate the ovule of the same hybrid pepper plant ALTATA. When crossed with another pepper plant, a hybrid seed is produced. Such methods of hybridization and self-pollination are well known to those skilled in the art of breeding.

An inbred pepper line such as one of the parental lines of hybrid pepper ALTATA has been produced through several cycles of self-pollination and is therefore to be considered as a homozygous line. An inbred line can also be produced though the dihaploid system which involves doubling the chromosomes from a haploid plant or embryo thus resulting in an inbred line that is genetically stable (homozygous) and can be reproduced without altering the inbred line. Haploid plants could be obtained from haploid embryos that might be produced from microspores, pollen, anther cultures or ovary cultures or spontaneous haploidy. The haploid embryos may then be doubled by chemical treatments such as by colchicine or be doubled autonomously. The haploid embryos may also be grown into haploid plants and treated to induce the chromosome doubling. In either case, fertile homozygous plants are obtained. A hybrid variety is classically created through the fertilization of an ovule from an inbred parental line by the pollen of another, different inbred parental line. Due to the homozygous state of the inbred line, the produced gametes carry a copy of each parental chromosome. As both the ovule and the pollen bring a copy of the arrangement and organization of the genes present in the parental lines, the genome of each parental line is present in the resulting F1 hybrid, theoretically in the arrangement and organization created by the plant breeder in the original parental line.

As long as the homozygosity of the parental lines is maintained, the resulting hybrid cross shall be stable. The F1 hybrid is then a combination of phenotypic characteristics issued from two arrangement and organization of genes, both created by a person skilled in the art through the breeding process.

Still further, this invention also is directed to methods for producing a pepper plant derived from hybrid pepper ALTATA by crossing hybrid pepper plant ALTATA with a second pepper plant. In some embodiments, the methods further comprise obtaining a progeny seed from the cross. In some embodiments, the methods further comprise growing the progeny seed, and possibly repeating the crossing and growing steps with the pepper hybrid plant ALTATA-derived plant from 0 to 7 or more times. Thus, any such methods using the hybrid pepper plant ALTATA are part of this invention: selfing, backcrosses, hybrid production, crosses to populations, and the like. All plants produced using hybrid pepper plant ALTATA as a parent are within the scope of this invention, including plants derived from hybrid pepper plant ALTATA. In some embodiments, such plants have one, more than one or all physiological and morphological characteristics of the pepper hybrid plant ALTATA listed in Table 1 including but not limited to as determined at the 5% significance level when grown in the same environmental conditions. In some embodiments, such plants might exhibit additional and desired characteristics or traits such as high seed yield, high seed germination, seedling vigor, early maturity, high fruit yield, ease of fruit setting, disease tolerance or resistance, lodging resistance and adaptability for soil and climate conditions. Consumer-driven traits, such as a preference for a given fruit size, fruit shape, fruit color, fruit texture, fruit taste, fruit firmness, fruit sugar content are other traits that may be incorporated into new pepper plants developed by this invention.

A pepper plant can also be propagated vegetatively. A part of the plant, for example a shoot tissue, is collected, and a new plant is obtained from the part. Such part typically comprises an apical meristem of the plant. The collected part is transferred to a medium allowing development of a plantlet, including for example rooting or development of shoots, or is grafted onto a pepper plant or a rootstock prepared to support growth of shoot tissue. This is achieved using methods well known in the art. Accordingly, in one embodiment, a method of vegetatively propagating a plant of the present invention comprises collecting a part of a plant according to the present invention, e.g. a shoot tissue, and obtaining a plantlet from said part. In one embodiment, a method of vegetatively propagating a plant of the present invention comprises: a) collecting tissue of a plant of the present invention; b) rooting said proliferated shoots to obtain rooted plantlets. In one embodiment, a method of vegetatively propagating a plant of the present invention comprises: a) collecting tissue of a plant of the present invention; b) cultivating said tissue to obtain proliferated shoots; c) rooting said proliferated shoots to obtain rooted plantlets. In one embodiment, such method further comprises growing a plant from said plantlets. In one embodiment, a fruit is harvested from said plant. In one embodiments, such fruits and plants have all the physiological and morphological characteristics of hybrid pepper designated ALTATA fruits and plants when grown in the same environmental conditions. In one embodiment, the fruit is processed into products such as canned pepper fruits and/or parts thereof, freeze dried or frozen fruit and/or parts thereof, fresh or prepared fruit and/or parts thereof or pastes, sauces, puree and the like.

The invention is also directed to the use of the hybrid pepper plant ALTATA in a grafting process. In one embodiment, the hybrid pepper plant ALTATA is used as the scion while in another embodiment, the hybrid pepper plant ALTATA is used as a rootstock.

In some embodiments, the present invention teaches a seed of hybrid pepper designated ALTATA, wherein a representative sample of seed of said hybrid is deposited under NCIMB No. 44199.

In some embodiments, the present invention teaches a pepper plant, or a part thereof, produced by growing the deposited ALTATA seed.

In some embodiments, the present invention teaches pepper plant parts, wherein the pepper part is selected from the group consisting of: a leaf, a flower, a fruit, a seed, an ovule, pollen, a cell, a rootstock, and a scion.

In some embodiments, the present invention teaches a pepper plant, or a part thereof, having all of the characteristics of hybrid ALTATA as listed in Table 1 of this application including but not limited to when grown in the same environmental conditions.

In some embodiments, the present invention teaches a pepper plant, or a part thereof, having all of the physiological and morphological characteristics of hybrid ALTATA, wherein a representative sample of seed of said hybrid was deposited under NCIMB No.

In some embodiments, the present invention teaches a tissue culture of regenerable cells produced from the plant or plant part grown from the deposited ALTATA seed, wherein cells of the tissue culture are produced from a plant part selected from the group consisting of protoplasts, embryos, meristematic cells, callus, pollen, ovules, flowers, seeds, leaves, roots, root tips, anthers, stems, petioles, fruits, axillary buds, cotyledons and hypocotyls. In some embodiments, the plant part includes protoplasts produced from a plant grown from the deposited ALTATA seed.

In some embodiments, the present invention teaches a composition comprising regenerable cells produced from the plant or plant part grown from the deposited hybrid ALTATA seed, or other plant part or plant cell. In some embodiments, the composition comprises a growth media. In some embodiments, the growth media is solid or a synthetic cultivation medium. In some embodiments, the composition is a pepper plant regenerated from the tissue culture from a plant grown from the deposited ALTATA seed, said plant having the characteristics of hybrid ALTATA, wherein a representative sample of seed of said hybrid is deposited under NCIMB No. 44199.

In some embodiments, the present invention teaches a pepper fruit produced from the plant grown from the deposited ALTATA seed. In one embodiments, such fruits have all the physiological and morphological characteristics of hybrid pepper designated ALTATA fruits when grown in the same environmental conditions.

In some embodiments, methods of producing said pepper fruit comprise a) growing the pepper plant from deposited ALTATA seed to produce a pepper fruit, and b) harvesting said pepper fruit. In some embodiments, the present invention also teaches a pepper fruit produced by the method of producing pepper fruit and/or seed as described above. In one embodiments, such fruits have all the physiological and morphological characteristics of fruits of hybrid pepper designated ALTATA (e.g. those listed in Table 1) when grown in the same environmental conditions.

In some embodiments, the present invention teaches methods for producing a pepper seed comprising crossing a first parent pepper plant with a second parent pepper plant and harvesting the resultant pepper seed, wherein said first parent pepper plant and/or second parent pepper plant is the pepper plant produced from the deposited ALTATA seed or a pepper plant having all of the characteristics of pepper hybrid ALTATA as listed in Table 1 including but not limited to when grown in the same environmental conditions.

In some embodiments, the present invention teaches methods for producing a pepper seed comprising self-pollinating the pepper plant grown from the deposited ALTATA seed and harvesting the resultant pepper seed.

In some embodiments, the present invention teaches the seed produced by any of the above described methods.

In some embodiments, the present invention teaches methods of vegetatively propagating the pepper plant grown from the deposited ALTATA seed, said method comprising a) collecting part of a plant grown from the deposited ALTATA seed and b) regenerating a plant from said part.

In some embodiments, the method further comprises harvesting a fruit and/or seed from said vegetatively propagated plant.

In some embodiments, the present invention teaches the plant and the fruit and/or seed of plants vegetatively propagated from plant parts of plants grown from the deposited ALTATA seed. In one embodiments, such plant, fruits and/or seeds have all the physiological and morphological characteristics of hybrid pepper designated ALTATA plant, fruits and/or seeds of pepper hybrid ALTATA (e.g. those listed in Table 1) when grown in the same environmental conditions.

In some embodiments, the present invention teaches methods of producing a pepper plant derived from the hybrid variety ALTATA. In some embodiment the methods comprise (a) self-pollinating the plant grown from the deposited ALTATA seed at least once to produce a progeny plant derived from pepper hybrid ALTATA. In some embodiments, the method further comprises (b) crossing the progeny plant derived from pepper hybrid ALTATA with itself or a second pepper plant to produce a seed of a progeny plant of a subsequent generation; and; (c) growing the progeny plant of the subsequent generation from the seed, and crossing the progeny plant of the subsequent generation with itself or a second pepper plant to produce a pepper plant derived from the hybrid pepper variety ALTATA. In some embodiments said methods further comprise the step of: (d) repeating steps b) and/or c) for at least 1, 2, 3, 4, 5, 6, 7, or more generation to produce a pepper plant derived from the hybrid pepper variety ALTATA.

In some embodiments, the present invention teaches methods of producing a pepper plant derived from the hybrid variety ALTATA, the methods comprising (a) crossing the plant grown from the deposited ALTATA seed with a second pepper plant to produce a progeny plant derived from pepper hybrid ALTATA. In some embodiments, the method further comprises; (b) crossing the progeny plant derived from pepper hybrid ALTATA with itself or a second pepper plant to produce a seed of a progeny plant of a subsequent generation; and; (c) growing the progeny plant of the subsequent generation from the seed; (d) crossing the progeny plant of the subsequent generation with itself or a second pepper plant to produce a pepper plant derived from the hybrid pepper variety ALTATA. In some embodiments said methods further comprise the steps of: (e) repeating step (b), (c) and/or (d) for at least 1, 2, 3, 4, 5, 6, 7 or more generation to produce a pepper plant derived from the hybrid pepper variety ALTATA.

In some embodiments, the present invention teaches plants grown from the deposited ALTATA seed wherein said plants comprise a single locus conversion. As used herein, the term "a" or "an" refers to one or more of that entity; for example, "a single locus conversion" refers to one or more single locus conversions or at least one single locus conversion. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements. In some embodiments said single locus conversion confers said plants with a trait selected from the group consisting of male sterility, male fertility, herbicide resistance, insect resistance, resistance for bacterial, fungal, mycoplasma or viral disease, enhanced plant quality such as improved drought or salt tolerance, water stress tolerance, improved standability, enhanced plant vigor, improved shelf life, delayed senescence or controlled ripening, increased nutritional quality such as increased sugar content or increased sweetness, increased texture, flavor and aroma, improved fruit length and/or size, protection for color, fruit shape, uniformity, length or diameter, refinement or depth lodging resistance, yield and recovery when compared to a suitable check plant. In some embodiments, the check plant is a pepper hybrid ALTATA not having said single locus conversion. In some embodiments, the at least one single locus conversion is an artificially mutated gene or a gene or nucleotide sequence modified through the use of New Breeding Techniques.

In some embodiments, the present invention provides a method of producing a commodity plant product comprising collecting the commodity plant product from the plant of the present invention. The commodity plant product produced by said method is also part of the present invention.

In addition to the exemplary aspects and embodiments described above, further aspects and embodiments will become apparent by study of the following descriptions.

DETAILED DESCRIPTION OF THE INVENTION

Definitions

In the description and tables that follow, a number of terms are used. In order to provide a clear and consistent understanding of the specification and claims, including the scope to be given such terms, the following definitions are provided: Adaptability. A plant that has adaptability is a plant able to grow well in different growing conditions (climate, soils, etc.).

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid F1 with one of the parental genotypes of the F1 hybrid.

Commodity plant product. A "commodity plant product" refers to any composition or product that is comprised of material derived from a plant, seed, plant cell, or plant part of the present invention. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, paper, tea, coffee, silage, crushed of whole grain, and any other food for human or animal consumption; and biomasses and fuel products; and raw material in industry.

Collection of seeds. In the context of the present invention a collection of seeds is a grouping of seeds mainly containing similar kind of seeds, for example hybrid seeds having the inbred line of the invention as a parental line, but that may also contain, mixed together with this first kind of seeds, a second, different kind of seeds, of one of the inbred parent lines, for example the inbred line of the present invention. A commercial bag of hybrid seeds having the inbred line of the invention as a parental line and containing also the inbred line seeds of the invention would be, for example such a collection of seeds.

Decreased vigor. A plant having a decreased vigor in the present invention is a plant that, compared to other plants has a less vigorous appearance for vegetative and/or reproductive characteristics including shorter plant height, small fruit size, fewer fruit or other characteristics.

Earliness. The earliness relates the number of fruits produced from 12 to 15 days following the beginning of the harvest: the more fruits produced, the more earliness of the plant Easy to pick fruit. A fruit that is easy to pick is a fruit that easily detaches from the plant. Once grabbed and twisted, the fruit will break between the peduncle and the stem. For fruits not easy to pick, the peduncle breaks off the fruits. A fruit that is easy to pick is also a fruit that is easily accessible for harvest. When plants have an open plant habit, the fruits are harvested more easily than when the plants have closed habit.

Enhanced nutritional quality. The nutritional quality of the pepper of the present invention can be enhanced by the introduction of several traits comprising a higher endosperm sugar content, flesh texture, brix, aroma content and increased sweetness, increased lycopene content of the peel, etc.

Essentially all the physiological and morphological characteristics. A plant having essentially all the physiological and morphological characteristics means a plant having the physiological and morphological characteristics of the recurrent parent, except for the characteristics derived from the converted gene.

Extended harvest. An extended harvest is a plant that produces fruits throughout the harvest season.

Flesh color: In the context of the present invention, the flesh color is the color of the pepper flesh.

Field holding ability: Field holding ability is the ability for fruit quality to maintain even after fruit is ripe (has turned red).

Grafting. Grafting is the operation by which a rootstock is grafted with a scion. The primary motive for grafting is to avoid damages by soil-born pest and pathogens when genetic or chemical approaches for disease management are not available. Grafting a susceptible scion onto a resistant rootstock can provide a resistant cultivar without the need to breed the resistance into the cultivar. In addition, grafting may enhance tolerance to abiotic stress, increase yield and result in more efficient water and nutrient uses.

Good Seed Producer. A plant is a good seed producer when it produces numerous seeds.

For pepper, a good seed producing plant will produce an average of 25 grams of seeds during the harvest season.

Immunity to disease(s) and or insect(s). A pepper plant which is not subject to attack or infection by specific disease(s) and or insect(s) is considered immune.

Industrial usage. The industrial usage of the pepper of the present invention comprises the use of the pepper fruit for consumption, whether as fresh products or in canning, freezing or any other industries.

Intermediate resistance to disease(s) and or insect(s). A pepper plant that restricts the growth and development of specific disease(s) and or insect(s), but may exhibit a greater range of symptoms or damage compared to a resistant plants. Intermediate resistant plants will usually show less severe symptoms or damage than susceptible plant varieties when grown under similar environmental conditions and/or specific disease(s) and or insect(s) pressure, but may have heavy damage under heavy pressure. Intermediate resistant pepper plants are not immune to the disease(s) and or insect(s).

Maturity. In the region of best adaptability, maturity is the number of days from transplanting to optimal time for fruit harvest.

New Breeding Techniques: New breeding techniques are said of various new technologies developed and/or used to create new characteristics in plants through genetic variation, the aim being targeted mutagenesis, targeted introduction of new genes or gene silencing (RdDM).

Example of such new breeding techniques are targeted sequence changes facilitated thru the use of Zinc finger nuclease (ZFN) technology (ZFN-1, ZFN-2 and ZFN-3, see U.S. Pat. No. 9,145,565, incorporated by reference in its entirety), Oligonucleotide directed mutagenesis (ODM), Cisgenesis and intragenesis, RNA-dependent DNA methylation (RdDM, which does not necessarily change nucleotide sequence but can change the biological activity of the sequence), Grafting (on GM rootstock), Reverse breeding, Agro-infiltration (agro-infiltration "sensu stricto", agro-inoculation, floral dip), Transcription Activator-Like Effector Nucleases (TALENs, see U.S. Pat. Nos. 8,586,363 and 9,181,535, incorporated by reference in their entireties), the CRISPR/Cas system (see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference), engineered meganuclease re-engineered homing endonucleases, DNA guided genome editing (Gao et al., Nature Biotechnology (2016), doi: 10.1038/nbt.3547, incorporated by reference in its entirety), and Synthetic genomics). A major part of today's targeted genome editing, another designation for New Breeding Techniques, is the applications to induce a DNA double strand break (DSB) at a selected location in the genome where the modification is intended. Directed repair of the DSB allows for targeted genome editing. Such applications can be utilized to generate mutations (e.g., targeted mutations or precise native gene editing) as well as precise insertion of genes (e.g., cisgenes, intragenes, or transgenes). The applications leading to mutations are often identified as site-directed nuclease (SDN) technology, such as SDN1, SDN2 and SDN3. For SDN1, the outcome is a targeted, non-specific genetic deletion mutation: the position of the DNA DSB is precisely selected, but the DNA repair by the host cell is random and results in small nucleotide deletions, additions or substitutions. For SDN2, a SDN is used to generate a targeted DSB and a DNA repair template (a short DNA sequence identical to the targeted DSB DNA sequence except for one or a few nucleotide changes) is used to repair the DSB: this results in a targeted and predetermined point mutation in the desired gene of interest. As to the SDN3, the SDN is used along with a DNA repair template that contains new DNA sequence (e.g. gene). The outcome of the technology would be the integration of that DNA sequence into the plant genome. The most likely application illustrating the use of SDN3 would be the insertion of cisgenic, intragenic, or transgenic expression cassettes at a selected genome location. A complete description of each of these techniques can be found in the report made by the Joint Research Center (JRC) Institute for Prospective Technological Studies of the European Commission in 2011 and titled "New plant breeding techniques—State-of-the-art and prospects for commercial development", which is incorporated by reference in its entirety.

Plant adaptability. A plant having good plant adaptability means a plant that will perform well in different growing conditions and seasons.

Plant cell. As used herein, the term "plant cell" includes plant cells whether isolated, in tissue culture, or incorporated in a plant or plant part.

Plant Part. As used herein, the term plant includes plant cells, plant protoplasts, plant cell tissue cultures from which pepper plants can be regenerated, plant calli, plant clumps and plant cells that are intact in plants or parts of plants, such as embryos, pollen, ovules, flowers, seeds, fruit, rootstock, scions, stems, roots, anthers, pistils, root tips, leaves, meristematic cells, axillary buds, hypocotyls cotyledons, ovaries, seed coat endosperm and the like. In some embodiments, the plant part at least comprises at least one cell of said plant. In some embodiments, the plant part is further defined as a pollen, a meristem, a cell or an ovule. In some embodiments, a plant regenerated from the plant part has all of the phenotypic and morphological characteristics of a pepper hybrid of the present invention, including but not limited to as determined at the 5% significance level when grown in the same environmental conditions.

Quantitative Trait Loci (QTL) Quantitative trait loci refer to genetic loci that control to some degree numerically representable traits that are usually continuously distributed.

Regeneration. Regeneration refers to the development of a plant from tissue culture.

Resistance to disease(s) and or insect(s). A pepper plant that restricts the growth and development of specific disease (s) and or insect(s) under normal disease(s) and or insect(s) attack pressure when compared to susceptible plants. These pepper plants can exhibit some symptoms or damage under heavy disease(s) and or insect(s) pressure. Resistant pepper plants are not immune to the disease(s) and or insect(s).

Rootstock. A rootstock is the lower part of a plant capable of receiving a scion in a grafting process.

Ribs. The ribs on the fruit may be prominent, inconspicuous or nonexistent. They refer to the ridges along the fruit mostly near the peduncle.

RHS. RHS refers to the Royal Horticultural Society of England which publishes an official botanical color chart quantitatively identifying colors according to a defined numbering system. The chart may be purchased from Royal Hort. Society Enterprise Ltd. RHS Garden; Wisley, Woking, Surrey GU236QB, UK.

Scion. A scion is the higher part of a plant capable of being grafted onto a rootstock in a grafting process.

Single gene converted (conversion). Single gene converted (conversion) plants refer to plants which are developed by a plant breeding technique called backcrossing wherein essentially all of the desired morphological and physiological characteristics of a plant are recovered in addition to the single gene transferred into the plant via the backcrossing technique or via genetic engineering. A single gene converted plant can also be referred to a plant obtained though mutagenesis or through the use of some new breeding techniques, whereas the single gene converted plant has essentially all of the desired morphological and physiological characteristics of the original variety in addition to the single gene or nucleotide sequence muted or engineered through the New Breeding Techniques.

Small plant. A small plant has short internodes with petiole lengths of approximately 40 cm and a plant height of 40 to 60 cm. It depends on how the plant spreads out horizontally or vertically.

Susceptible to disease(s) and or insect(s). A pepper plant that is susceptible to disease(s) and or insect(s) is defined as a pepper plant that has the inability to restrict the growth and development of specific disease(s) and or insect(s). Plants that are susceptible will show damage when infected and are more likely to have heavy damage under moderate levels of specific disease(s) and or insect(s).

Tolerance to abiotic stresses. A pepper plant that is tolerant to abiotic stresses has the ability to endure abiotic stress without serious consequences for growth, appearance and yield.

Uniformity. Uniformity, as used herein, describes the similarity between plants or plant characteristics which can be a described by qualitative or quantitative measurements.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants).

Yield (Unit Vol./Acre). The yield in units/acre is the actual yield of the pepper at harvest.

Pepper Plants

The term pepper as used in agriculture may refer to quite different plant species. For example, some plants in the genera Piper, *Capsicum*, Pimenta, Zanthoxylum, *Schinus*, and several other species are called pepper. As used herein, the term pepper mainly refers to a plant species in the *Capsicum* genus, unless specified otherwise.

*Capsicum* is a genus of flowering plants in the Solanaceae family. Its species are native to the Americas, where they have been cultivated for thousands of years by the people of the tropical Americas, and are now cultivated worldwide. Some of the members of *Capsicum* are used as spices, vegetables, and medicines. The fruit of *Capsicum* plants have a variety of names depending on geographic location and fruit shape or type. They are commonly called chili pepper, red or green pepper, or sweet pepper in Britain, and typically called just *capsicum* in Australia, New Zealand, and Indian English. The large mild form is called bell pepper in the U.S. and Canada. They are called paprika in some other countries (although, somewhat confusingly, paprika can also refer to the powdered spice made from various *capsicum* fruit).

The fruit of most species of *Capsicum* contain capsaicin (methyl vanillyl nonenamide), a lipophilic chemical that can produce a strong burning sensation in the mouth of the unaccustomed eater. The secretion of capsaicin protects the fruit from consumption by mammals while the bright colors attract birds that will disperse the seeds. Capsaicin is present in largest quantities in the placental tissue (which holds the seeds), the internal membranes and, to a lesser extent, the other fleshy parts of the fruits of plants in the genus *Capsicum*. The seeds themselves do not produce any capsaicin, although the highest concentration of capsaicin can be found in the white pith around the seeds. The amount of capsaicin in Capsicums is highly variable and dependent on genetics, giving almost all types of Capsicums varied amounts of perceived heat. The only *Capsicum* without capsaicin is the bell pepper, a cultivar of *Capsicum annuum*, which has a zero rating on the Scoville scale. The lack of capsaicin in bell peppers is due to a recessive gene that eliminates capsaicin and, consequently, the "hot" taste usually associated with the rest of the *Capsicum* family.

Chili peppers are of great importance in Native American medicine, and capsaicin is used in modern medicine— mainly in topical medications—as a circulatory stimulant and analgesic. In more recent times, an aerosol extract of capsaicin, usually known as *capsicum* or pepper spray, has become widely used by police forces as a non-lethal means of incapacitating a person, and in a more widely dispersed form for riot control, or by individuals for personal defense. Although black pepper and Sichuan pepper cause similar burning sensations, they are caused by different substances—piperine and hydroxy-alpha sanshool, respectively.

Non-limiting exemplary *Capsicum* species include, *C. annuum, C. frutescens, C. chinense, C. pendulum, C. pubescens, C. minimum, C. baccatum, C. abbreviatum, C. anomalum, C. breviflorum, C. buforum, C. brasilianum, C. campylopodium, C. cardenasii, C. chacoense, C. ciliare, C. ciliatum, C. chlorocladium, C. coccineum, C. cordiforme, C. cornutum, C. dimorphum, C. dusenii, C. exile, C. eximium, C. fasciculatum, C. fastigiatum, C. flexuosum, C. galapa-*

*goense, C. geminifolum, C. hookerianum, C. lanceolatum, C. leptopodum, C. luteum, C. microcarpum, C. minutiflorum, C. mirabile, C. parvifolium, C. praetermissum, C. schottianum, C. scolnikianum, C. stramonfolium, C. tetragonum, C. tovarii, C. villosum,* and *C. violaceum*. More *Capsicum* species are described in Heiser and Smith (The cultivated *Capsicum* peppers. Econ Bot 7:214-227), Pickersgill (1988, The genus *Capsicum*: a multidisciplinary approach to the taxonomy of cultivated and wild plants. Biologisches Zentralblatt 107:381-389), De (*Capsicum*: the genus *Capsicum*, Volume 33 of Medicinal and aromatic plants, Publisher CRC Press, 2003, ISBN 0415299918, 9780415299916), Bosland and Votava (Peppers: vegetable and spice capsicums, Issue 12 of Crop production science in horticulture, Publisher CABI, 2000, ISBN 0851993354, 9780851993355), and Andrews (Peppers: the domesticated Capsicums, Publisher University of Texas Press, 1995, ISBN 0292704674, 9780292704671).

*Capsicum* species have been characterized based on morphology, isozyme analysis, cytology, hybridization, restriction fragment length polymorphism (RFLP), amplified fragment length polymorphism (AFLP), random amplified polymorphic DNA (RAPD), sequence specific amplification polymorphism (S-SAP), simple sequence repeat length polymorphism (SSRLP), inter-simple sequence repeats (ISSR), cleaved amplified polymorphic sequence (CAPS), and direct or directed amplification of minisatellite region DNA amplified using the polymerase chain reaction (DAMD-PCR), for the identification of genotypes or accessions at the taxonomic level, assessment of the relative diversity or similarity within and between species, and selection of diverse accessions with desirable traits for breeding purposes (Eshbaugh 1993; Prince et al. 1992; Rodriguez et al. 1999; Lefebvre et al. 2001; Adetula 2006; Guzman et al. 2005; Ince et al. 2009).

Most *Capsicum* species are diploid (2n=2×=24), but there are a few species for which the genome is 2n=2×=32. *Capsicum* has a large genome, with the DNA content ranging from 7.65 pg/nucleus in *C. annuum* to 9.72 pg/nucleus in *C. pubescens*, and with a general mean of 8.42 pg/nucleus. *Capsicum* genes have been studied for almost a century since 1912, and a list of genes and related traits are described by Wang (2006, The Genes of *Capsicum*, HortScience 41(5) 1169-1187), which is incorporated by reference in its entirety.

Enzymatic studies of *Capsicum* (Jensen et al., *Taxon*, 28:315-327, 1979; McLeod et al, 1979a (Bull Torrey Bot Club 106:326-333.), 1979b (Pages 701-713 in JG Hawkes, RN Lester, AD Skelding, eds. The biology and taxonomy of the Solanaceae. Academic Press, London), 1982 (Econ Bot 36:361-368), and 1983 (Evolution 37:562-574)) have demonstrated that *Capsicum* species can be grouped into three taxonomic categories (*Capsicum annuum* complex, *Capsicum baccatum* complex, and *Capsicum eximium* complex) that somewhat agreed with groupings based on flower color.
*Capsicum annuum*

*Capsicum annum* is a domesticated species of the plant genus *Capsicum* native to South America and it is now cultivated worldwide. Despite being a single species, the *Capsicum annuum* has many forms, with a variety of names, even in the same language. In American English it is commonly known as the chili pepper, although not all varieties would be recognized by most speakers under this name. In British English, the sweet varieties are called peppers and the hot varieties are called chilies, whereas in Australian English the name *capsicum* is commonly used for bell peppers exclusively and chili is often used to encompass the hotter varieties. Its forms are varied, from large to small, sweet to sour, very hot to bland.

The plant is a herbaceous annual, with a densely branched stem. The plant reaches 0.5-1.5 m (20-60 in). Single white flowers bear the fruit which is green when unripe, changing principally to red, although some varieties may ripen to brown or purple. While the species can tolerate most climates, they are especially productive in warm and dry climates.

Non-limiting exemplary *Capsicum annuum* varieties include, Aleppo, Anaheim, Bell, Cascabel, Cayenne, Cherry, Chilaca, Chiltepin, Cubanelle, De árbol, Fresno, Guajillo, Guntur, Sannam, Hungarian wax, Italian sweet pepper, Jalapeño, Japanese, Mirasol, Macho, New Mexico, Pepperoncini, Pequin pepper, Poblano, Puya, Serrano, Super Chili, and Tien Tsin.
Bell Pepper Bell pepper or sweet pepper or sweet bell pepper is a cultivar group of the species *Capsicum annuum*. Cultivars of the plant produce fruits in different colors, for example, green, red, yellow, orange, white, purple, and rainbow, depending on when they are harvested and the specific cultivar. The term "bell pepper" is often used for any of the large bell shaped *capsicum* fruits, regardless of their color. As used herein, the phrase "bell pepper" is equivalent to "blocky type pepper" or "blocky shape pepper", as this term is understood by those skilled in the art of pepper breeding and pepper production. The fruit is also frequently consumed in its unripe form, when the fruit is still green.

In the United States and Canada, in addition to the terms "bell pepper" and "sweet pepper," the fruit is often referred to simply as a "pepper" or referred to by color (e.g. "red pepper", "green pepper", "yellow pepper"), although the more specific term "bell pepper" is understood in most regions. In parts of Indiana, Ohio, and Pennsylvania, the fruit is called a "mango". The origin of this use is in the use of the term "mango" or "mangoed" to refer to pickled fruits. At a certain time, mangoes were available in the United States only in pickled form. Later, it became common in these regions to use bell peppers in pickled form, thus the term "mangoed peppers" or "mango peppers" later shortened to "mangoes."

Green peppers are less sweet and slightly bitter than red, yellow or orange peppers. The taste of ripe peppers can also vary with growing conditions and post-harvest storage treatment; the sweetest are fruit allowed to ripen fully on the plant in full sunshine, while fruit harvested green and after-ripened in storage are less sweet. Compared to green peppers, red peppers have more vitamins and nutrients and contain the antioxidant lycopene. The level of carotene, another antioxidant, is nine times higher in red peppers. Red peppers also have twice the vitamin C content of green peppers. Orange bell peppers (or paprikas) contain even more vitamin C and significantly more vitamin A. Orange bell peppers are both juicy and sweet, and because they contain less than half the calories of an orange, orange bell peppers are pre-eminently appropriate as a refreshing, low-calorie food, both raw and prepared in any dish. They can be eaten raw without having indigestion later.

Hybrid vigor has been documented in peppers and hybrids are gaining more and more popularity amongst farmers with uniformity of plant characteristics.

Hybrid commercial pepper seed can be produced by hand pollination. Pollen of the male parent is harvested and manually applied to the stigmatic surface of the female inbred. Prior to and after hand pollination, flowers are covered so that insects do not bring foreign pollen and create a mix or impurity. Flowers are tagged to identify pollinated fruit from which seed will be harvested There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm.

In pepper, these important traits may include increased fruit number, fruit size and fruit weight, higher seed yield, improved color, resistance to pest, diseases and insects, tolerance to drought and heat, better uniformity, higher nutritional value and better agronomic quality such as favorable plant structure, flesh color or texture, firmness, growth rate, high seed germination, seedling vigor, early fruit setting, ease of fruit setting, adaptability for soil and climate conditions. With mechanical harvesting of processing pepper, fruit setting concentration, harvestability and field holding are also very important.

In some embodiments, particularly desirable traits that may be incorporated by this invention are improved resistance to different viral, fungal, and bacterial pathogens. Important diseases include but are not limited to Tobacco Mosaic Virus, (caused by Tobamovirus Pathotype 0), Tomato Mosaic Virus (caused by Tobamovirus Pathotype 1-2), Pepper Mild Mottle Virus (caused by Tobamovirus Pathotype 1-2-3), Potato Virus Y (caused by Potato Virus Y Pathotype 0, 1 or 1-2), *Phytophthora* (caused by *Phytophthora capsici*), Cucumber Mosaic Virus, Tomato Spotted Wilt Virus, Bacterial Spot (caused by *Xanthomonas campestris* pv. *vesicatoria*, multiple races). Improved resistance to insect pests is another desirable trait that may be incorporated into new pepper plants developed by this invention. Insect pests affecting the various species of pepper include, but not limited to arthropod pests such as *Tuta absoluta, Franklienella occidentalis, Bemisia tabaci*, etc.

Other desirable traits include traits related to improved pepper fruits. A non-limiting list of fruit phenotypes used during breeding selection include:

Intensity of Color at Green Stage. The color at green stage is the measure of the color prior to physiological maturity and is typically the stage when fruit have reached full size and firmness to be harvested for commercial sales. It ranges between very light green to very dark green.

pH. The pH is a measure of acidity of the fruit puree. A pH under 4.5 is desirable to prevent bacterial spoilage of finished products. pH rises as fruit matures.

Fruit Color. Fruit color is measured as Hunters a/b ratio, where a represents red/green, positive values are red, negative values are green and 0 is neutral; b represents yellow/blue, where positive values are yellow, negative values are blue and 0 is neutral; a/b represents the intense of redness: large value represents deep red color, small value represents light or yellowish red color.

Fruit Shape. Fruit shape is the overall shape of the intact fruit and ranges from pointed to blocky.

Fruit Weight. The weight of a single fruit or the average of many fruit measured at harvest maturity and recorded in a convenient unit of measure.

Fruit firmness. The fruit firmness is the resistance to penetration and is measured using a Digital Durometer Model DD-4-00 (Rex Gauge Company, Buffalo Grove, IL, USA). Durometer readings are taken at 4 locations (each about 90 degrees apart) on the approximate mid-point of a pepper, with the pepper laying on its side. From a fruit sample collected at a given location, the resistance to penetration is measured with the durometer from 9 individual fruit at 4 locations per fruit (a total of 36 independent measurements). The P5 value is calculated from the following equation: D-39/10, where D is the value from the Durometer.

Fruit Glossiness. Fruit glossiness is a measure of the reflectance of the fruit surface and ranges from very weak (dull) to very strong (shiny).

Fruit Texture. Fruit texture is the measure of the surface texture of the fruit which can range from smooth to strongly wrinkled.

Plant Cover. Plant cover describes the extent of the outer layer of leaves of an individual plant. The relative area of the leaves covering or forming a canopy of leaves to cover the fruit and provide protection from direct sunlight. Scores range from very poor cover to heavy cover.

Pepper Breeding

The goal of pepper breeding is to develop new, unique and superior pepper inbred lines and hybrids. The breeder initially selects and crosses two or more parental lines, followed by repeated selfing and selection, producing many new genetic combinations. Another method used to develop new, unique and superior pepper inbred lines and hybrids occurs when the breeder selects and crosses two or more parental lines followed by haploid induction and chromosome doubling that result in the development of dihaploid inbred lines. The breeder can theoretically generate billions of different genetic combinations via crossing, selfing and mutations and the same is true for the utilization of the dihaploid breeding method.

During the development of new pepper inbreds and hybrids, the pepper breeder uses pepper plants, but also non-commercial pepper plants, such as plants that may contain characteristics that the breeder has interest in having in its pepper inbreds and hybrids. Such non-commercial pepper plants could be wild relatives of pepper species.

Each year, the plant breeder selects the germplasm to advance to the next generation. This germplasm is grown under unique and different geographical, climatic and soil conditions, and further selections are then made, during and at the end of the growing season. The inbred lines developed are unpredictable. This unpredictability is because the breeder's selection occurs in unique environments, with no control at the DNA level (using conventional breeding procedures or dihaploid breeding procedures), and with millions of different possible genetic combinations being generated. A breeder of ordinary skill in the art cannot predict the final resulting lines he develops, except possibly in a very broad and general fashion. This unpredictability results in the expenditure of large research monies to develop superior new pepper inbred lines and hybrids.

The development of commercial pepper hybrids requires the development of homozygous inbred lines, the crossing of these lines, and the evaluation of the F1 hybrid crosses.

Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes or through the dihaploid breeding method followed by the selection of desired phenotypes. The new inbreds are crossed with other inbred lines and the hybrids from these crosses are evaluated to determine which have commercial potential.

Choice of breeding or selection methods depends on the mode of plant reproduction, the heritability of the trait(s) being improved, and the type of cultivar used commercially (e.g., F1 hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

i Pedigree Selection

Pedigree breeding is used commonly for the improvement of self-pollinating crops or inbred lines of cross-pollinating crops. Two parents possessing favorable, complementary traits are crossed to produce an $F_1$. An $F_2$ population is produced by selfing one or several $F_1$s or by intercrossing two $F_1$s (sib mating). The dihaploid breeding method could also be used. Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential use as parents of new hybrid cultivars. Similarly, the development of new inbred lines through the dihaploid system requires the selection of the best inbreds followed by two to five years of testing in hybrid combinations in replicated plots.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In a multiple-seed procedure, breeders commonly harvest one or more fruit containing seed from each plant in a population and blend them together to form a bulk seed lot. Part of the bulked seed is used to plant the next generation and part is put in reserve. The procedure has been referred to as modified single-seed descent or the bulk technique.

The multiple-seed procedure has been used to save labor at harvest. It is considerably faster than removing one seed from each fruit by hand for the single seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

ii Backcross Breeding

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype recurrent parent and the trait of interest from the donor parent are selected and repeatedly crossed (backcrossed) to the recurrent parent. The resulting plant is expected to have the attributes of the recurrent parent (e.g., cultivar) and the desirable trait transferred from the donor parent.

When the term hybrid pepper plant is used in the context of the present invention, this also includes any hybrid pepper plant where one or more desired trait has been introduced through backcrossing methods, whether such trait is a naturally occurring one, a mutant, a transgenic one or a gene or a nucleotide sequence modified by the use of New Breeding Techniques. Backcrossing methods can be used with the present invention to improve or introduce one or more characteristic into the inbred parental line, thus potentially introducing these traits in to the hybrid pepper plant of the present invention. The term "backcrossing" as used herein refers to the repeated crossing of a hybrid progeny back to the recurrent parent, i.e., backcrossing one, two, three, four, five, six, seven, eight, nine, or more times to the recurrent parent. The parental pepper plant which contributes the gene or the genes for the desired characteristic is termed the nonrecurrent or donor parent. This terminology refers to the fact that the nonrecurrent parent is used one time in the backcross protocol and therefore does not recur. The parental pepper plant to which the gene or genes from the nonrecurrent parent are transferred is known as the recurrent parent as it is used for several rounds in the backcrossing protocol.

In a typical backcross protocol, the original inbred of interest (recurrent parent) is crossed to a second inbred (nonrecurrent parent) that carries the gene or genes of interest to be transferred. The resulting progeny from this cross are then crossed again to the recurrent parent and the process is repeated until a pepper plant is obtained wherein all the desired morphological and physiological characteristics of the recurrent parent are recovered in the converted plant, generally determined at a 5% significance level when grown in the same environmental conditions, in addition to the gene or genes transferred from the nonrecurrent parent. It has to be noted that some, one, two, three or more, self-pollination and growing of population might be included between two successive backcrosses. Indeed, an appropriate selection in the population produced by the self-pollination, i.e. selection for the desired trait and physiological and morphological characteristics of the recurrent parent might be equivalent to one, two or even three additional backcrosses in a continuous series without rigorous selection, saving then time, money and effort to the breeder. A non-limiting example of such a protocol would be the following: a) the first generation F1 produced by the cross of the recurrent parent A by the donor parent B is backcrossed to parent A, b) selection is practiced for the plants having the desired trait of parent B, c) selected plant are self-pollinated to produce a population of plants where selection is practiced for the plants having the desired trait of parent B and physiological and morphological characteristics of parent A, d) the selected plants are backcrossed one, two, three, four, five, six, seven, eight, nine, or more times to parent A to produce selected backcross progeny plants comprising the desired trait of parent B and the physiological and morphological characteristics of parent A. Step (c) may or may not be repeated and included between the backcrosses of step (d).

The selection of a suitable recurrent parent is an important step for a successful backcrossing procedure. The goal of a backcross protocol is to alter or substitute one or more trait(s) or characteristic(s) in the original inbred parental line in order to find it then in the hybrid made thereof. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important that the identification of the character(s) in the segregating population. In this instance it may then be necessary to introduce a test of the progeny to determine if the desired characteristic(s) has been successfully transferred. Such tests encompass visual inspection, simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as pepper leaf curl virus resistance in pepper, requires selfing the progeny or using molecular markers to determine which plant carry the recessive allele(s).

Many single gene traits have been identified that are not regularly selected for in the development of a new parental inbred of a hybrid pepper plant according to the invention but that can be improved by backcrossing techniques. Single gene traits may or may not be transgenic. Examples of these traits include but are not limited to, resistance for bacterial, fungal, or viral disease (gene Zym-0 for resistance to Zucchini Yellow Mosaic Virus (ZYMV)), agronomic traits, such as leaf silvering and fruit color, such as green, yellow, white or grey. These genes are generally inherited through the nucleus.

In 1981, the backcross method of breeding counted for 17% of the total breeding effort for inbred line development in the United States, accordingly to, Hallauer, A. R. et al. (1988) "Corn Breeding" Corn and Corn Improvement, No. 18, pp. 463-481.

The backcross breeding method provides a precise way of improving varieties that excel in a large number of attributes but are deficient in a few characteristics. (Page 150 of the Pr. R. W. Allard's 1960 book, published by John Wiley & Sons, Inc., *Principles of Plant Breeding*). The method makes use of a series of backcrosses to the variety to be improved during which the character or the characters in which improvement is sought is maintained by selection. At the end of the backcrossing the gene or genes being transferred unlike all other genes, will be heterozygous. Selfing after the last backcross produces homozygosity for this gene pair(s) and, coupled with selection, will result in a parental line of a hybrid variety with exactly or essentially the same adaptation, yielding ability and quality characteristics of the recurrent parent but superior to that parent in the particular characteristic(s) for which the improvement program was undertaken. Therefore, this method provides the plant breeder with a high degree of genetic control of his work.

The method is scientifically exact because the morphological and agricultural features of the improved variety could be described in advance and because a similar variety could, if it were desired, be bred a second time by retracing the same steps (Briggs, "Breeding wheats resistant to bunt by the backcross method", 1930 *Jour. Amer. Soc. Agron.*, 22: 289-244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be theoretically modified only with regards to genes being transferred, which are maintained in the population by selection.

Successful backcrosses are, for example, the transfer of stem rust resistance from 'Hope' wheat to 'Bart wheat' and even pursuing the backcrosses with the transfer of bunt resistance to create 'Bart 38', having both resistances. Also highlighted by Allard is the successful transfer of mildew, leaf spot and wilt resistances in California Common alfalfa to create 'Caliverde'. This new 'Caliverde' variety produced through the backcross process is indistinguishable from California Common except for its resistance to the three named diseases.

One of the advantages of the backcross method is that the breeding program can be carried out in almost every environment that will allow the development of the character being transferred or when using molecular markers that can identify the trait of interest.

The backcross technique is not only desirable when breeding for disease resistance but also for the adjustment of morphological characters, color characteristics and simply inherited quantitative characters such as earliness, plant height and seed size and shape. In this regard, a medium grain type variety, 'Calady', has been produced by Jones and Davis. As dealing with quantitative characteristics, they selected the donor parent with the view of sacrificing some of the intensity of the character for which it was chosen, i.e. grain size. 'Lady Wright', a long grain variety was used as the donor parent and 'Coloro', a short grain one as the recurrent parent. After four backcrosses, the medium grain type variety 'Calady' was produced.

iii Open-Pollinated Populations

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity.

Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement.

First, there is the situation in which a population is changed en masse by a chosen selection procedure. The outcome is an improved population that is indefinitely propagated by random-mating within itself in isolation.

Second, the synthetic variety attains the same end result as population improvement, but is not itself propagated as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

A) Mass Selection

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

B) Synthetics

A synthetic variety is produced by intercrossing a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or more cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

iv. Hybrids

A hybrid is an individual plant resulting from a cross between parents of differing genotypes. Commercial hybrids are now used extensively in many crops, including corn (maize), sorghum, sugarbeet, sunflower broccoli and tomato. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

Hybrid commercial pepper seed is produced by controlled hand pollination. The male flowers from the male plants are harvested and used to pollinate the stigmatic surface of the female flowers on the female plants. Prior to, and after hand pollination, flowers are covered so that insects do not bring foreign pollen and create a mix or impurity. Flowers are tagged to identify pollinated fruit from which seed will be harvested.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the F1 progeny. A double-cross hybrid is produced from four inbred lines crossed in pairs (A×B and C×D) and then the two F1 hybrids are crossed again (A×B)×(C×D). Much of the hybrid vigor and uniformity exhibited by F1 hybrids is lost in the next generation (F2). Consequently, seed from F2 hybrid varieties is not used for planting stock.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

v. Bulk Segregation Analysis (BSA)

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the*

National Academy of Sciences, USA, 99:9828-9832) and Quarrie et al. (Quarrie et al., 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs, SNPs or SSRs). Markers linked to the phenotype can be identified and used for breeding or QTL mapping.

vi. Hand-Pollination Method

Hand pollination describes the crossing of plants via the deliberate fertilization of female ovules with pollen from a desired male parent plant. In some embodiments the donor or recipient female parent and the donor or recipient male parent line are planted in the same field. The inbred male parent can be planted earlier than the female parent to ensure adequate pollen supply at the pollination time. In some embodiments, the male parent and female parent can be planted at a ratio of 1 male parent to 4-10 female parents. The male parent may be planted at the top of the field for efficient male flower collection during pollination. Pollination is started when the female parent flower is ready to be fertilized. Female flower buds that are ready to open in the following days are identified, covered with paper cups or small paper bags that prevent bee or any other insect from visiting the female flowers, and marked with any kind of material that can be easily seen the next morning. In some embodiments, this process is best done in the afternoon. The male flowers of the male parent are collected in the early morning before they are open and visited by pollinating insects. The covered female flowers of the female parent, which have opened, are un-covered and pollinated with the collected fresh male flowers of the male parent, starting as soon as the male flower sheds pollen. The pollinated female flowers are again covered after pollination to prevent bees and any other insects visit. The pollinated female flowers are also marked. The marked fruits are harvested. In some embodiments, the male pollen used for fertilization has been previously collected and stored.

vii. Bee-Pollination Method

Using the bee-pollination method, the parent plants are usually planted within close proximity. In some embodiments more female plants are planted to allow for a greater production of seed. Breeding of dioecious species can also be done by growing equal amount of each parent plant. Insects are placed in the field or greenhouses for transfer of pollen from the male parent to the female flowers of the female parent.

viii. Targeting Induced Local Lesions in Genomes (TILLING)

Breeding schemes of the present application can include crosses with TILLING® plant lines. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. As DNA bases are not pairing at the mismatch of the two DNA strands (the induced mutation in TILLING® or the natural mutation or SNP in EcoTILLING), they provoke a shape change in the double strand DNA fragment which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus*; John Innes Centre (UK), focusing on *Brassica rapa*; Fred Hutchinson Cancer Research, focusing on *Arabidopsis*; Southern Illinois University (USA), focusing on Soybean; John Innes Centre (UK), focusing on Lotus and *Medicago*; and INRA (France), focusing on Pea and Tomato.

More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

Thus in some embodiments, the breeding methods of the present disclosure include breeding with one or more TILLING plant lines with one or more identified mutations.

viii Mutation Breeding

Mutation breeding is another method of introducing new variation and subsequent traits into pepper plants. Mutations that occur spontaneously or are artificially induced can be useful sources of variability for a plant breeder. The goal of artificial mutagenesis is to increase the rate of mutation for a desired characteristic. Mutation rates can be increased by many different means or mutating agents including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in W. R. Fehr, 1993, Principles of Cultivar Development, Macmillan Publishing Co.

New breeding techniques such as the ones involving the uses of Zinc Finger Nucleases or oligonucleotide directed mutagenesis shall also be used to generate genetic variability and introduce new traits into pepper varieties.

ix. Double Haploids and Chromosome Doubling

One way to obtain homozygous plants without the need to cross two parental lines followed by a long selection of the segregating progeny, and/or multiple backcrossing is to produce haploids and then double the chromosomes to form doubled haploids. Haploid plants can occur spontaneously, or may be artificially induced via chemical treatments or by crossing plants with inducer lines (Seymour et al. 2012, PNAS vol. 109, pg. 4227-4232; Zhang et al., 2008 Plant Cell Rep. Dec. 27(12) 1851-60). The production of haploid progeny can occur via a variety of mechanisms which can affect the distribution of chromosomes during gamete formation. The chromosome complements of haploids sometimes double spontaneously to produce homozygous doubled haploids (DHs). Mixoploids, which are plants which contain cells having different ploidies, can sometimes arise and may represent plants that are undergoing chromosome doubling so as to spontaneously produce doubled haploid tissues, organs, shoots, floral parts or plants. Another common technique is to induce the formation of double haploid plants with a chromosome doubling treatment such as colchicine (El-Hennawy et al., 2011 Vol 56, issue 2 pg. 63-72; Doubled Haploid Production in Crop Plants 2003 edited by Maluszynski ISBN 1-4020-1544-5). The production of doubled haploid plants yields highly uniform inbred lines and is especially desirable as an alternative to sexual inbreeding of longer-generation crops. By producing doubled haploid progeny, the number of possible gene combinations for inherited traits is more manageable. Thus, an efficient doubled haploid technology can significantly reduce the time and the cost of inbred and cultivar development.

x. Protoplast Fusion

In another method for breeding plants, protoplast fusion can also be used for the transfer of trait-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits.

xi. Embryo Rescue

Alternatively, embryo rescue may be employed in the transfer of resistance-conferring genomic material from a donor plant to a recipient plant. Embryo rescue can be used as a procedure to isolate embryos from crosses to rapidly move to the next generation of backcrossing or selfing or wherein plants fail to produce viable seed. In this process, the fertilized ovary or immature seed of a plant is tissue cultured to create new plants (see Pierik, 1999, *In Vitro Culture of Higher Plants*, Springer, ISBN 079235267, 9780792352679, which is incorporated herein by reference in its entirety).

Grafting

Grafting is a process that has been used for many years in crops such as *cucurbitacea*, but only more recently for some commercial tomato production. Grafting may be used to provide a certain level of resistance to telluric pathogens such as *Phytophthora* or to certain nematodes. Grating is therefore intended to prevent contact between the plant or variety to be cultivated and the infested soil. The variety of interest used as the graft or scion, optionally an F1 hybrid, is grafted onto the resistant plant used as the rootstock. The resistant rootstock remains healthy and provides, from the soils, the normal supply for the graft that it isolates from the diseases. In some recent developments, it has also been shown that some rootstocks are also able to improve the agronomic value for the grafted plant and in particular the equilibrium between the vegetative and generative development that are always difficult to balance in pepper cultivation. See for example US 20140096289 that describes such improved rootstock pepper plant.

Breeding Evaluation

Each breeding program can include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s). The best lines are candidates for use as parents in new commercial cultivars; those still deficient in a few traits may be used as parents to produce new populations for further selection or in a backcross program to improve the parent lines for a specific trait.

In one embodiment, the plants are selected on the basis of one or more phenotypic traits. Skilled persons will readily appreciate that such traits include any observable characteristic of the plant, including for example growth rate, vigor, plant health, maturity, branching, plant height, leaf coverage, weight, color, taste, smell, changes in the production of one or more compounds by the plant (including for example, metabolites, proteins, drugs, carbohydrates, oils, and any other compounds).

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

It should be appreciated that in certain embodiments, plants may be selected based on the absence, suppression or inhibition of a certain feature or trait (such as an undesirable feature or trait) as opposed to the presence of a certain feature or trait (such as a desirable feature or trait).

Selecting plants based on genotypic information is also envisaged (for example, including the pattern of plant gene expression, genotype, or presence of genetic markers). Where the presence of one or more genetic marker is assessed, the one or more marker may already be known and/or associated with a particular characteristic of a plant; for example, a marker or markers may be associated with an increased growth rate or metabolite profile. This information could be used in combination with assessment based on other characteristics in a method of the disclosure to select for a combination of different plant characteristics that may be desirable. Such techniques may be used to identify novel quantitative trait loci (QTLs). By way of example, plants may be selected based on growth rate, size (including but not limited to weight, height, leaf size, stem size, branching pattern, or the size of any part of the plant), general health, survival, tolerance to adverse physical environments and/or any other characteristic, as described herein before.

Further non-limiting examples include selecting plants based on: speed of seed germination; quantity of biomass produced; increased root, and/or leaf/shoot growth that leads to an increased yield (fruit) or biomass production; effects on plant growth that results in an increased seed yield for a crop; effects on plant growth which result in an increased yield; effects on plant growth that lead to an increased resistance or tolerance to disease including fungal, viral or bacterial diseases, to mycoplasma, or to pests such as insects, mites or nematodes in which damage is measured by decreased foliar symptoms such as the incidence of bacterial or fungal lesions, or area of damaged foliage or reduction in the numbers of nematode cysts or galls on plant roots, or improvements in plant yield in the presence of such plant pests and diseases; effects on plant growth that lead to increased metabolite yields; effects on plant growth that lead to improved aesthetic appeal which may be particularly important in plants grown for their form, color, for example the color intensity of pepper exocarp (skin) of said fruit.

Molecular Breeding Evaluation Techniques

Selection of plants based on phenotypic or genotypic information may be performed using techniques such as, but not limited to: high through-put screening of chemical components of plant origin, sequencing techniques including high through-put sequencing of genetic material, differential display techniques (including DDRT-PCR, and DD-PCR), nucleic acid microarray techniques, RNA-seq (Transcriptome Sequencing), qRTPCR (quantitative real time PCR).

In one embodiment, the evaluating step of a plant breeding program involves the identification of desirable traits in progeny plants. Progeny plants can be grown in, or exposed to conditions designed to emphasize a particular trait (e.g. drought conditions for drought tolerance, lower temperatures for freezing tolerant traits). Progeny plants with the highest scores for a particular trait may be used for subsequent breeding steps.

In some embodiments, plants selected from the evaluation step can exhibit a 1%, 5%, 10%, 15%, 20%, 25%, 30%, 35%, 40%, 45%, 50%, 55%, 60%, 65%, 70%, 75%, 80%, 85%, 90%, 95%, 100%, 120% or more improvement in a particular plant trait compared to a control plant.

In other embodiments, the evaluating step of plant breeding comprises one or more molecular biological tests for genes or other markers. For example, the molecular biological test can involve probe hybridization and/or amplification of nucleic acid (e.g., measuring nucleic acid density by Northern or Southern hybridization, PCR) and/or immunological detection (e.g., measuring protein density, such as precipitation and agglutination tests, ELISA (e.g., Lateral Flow test or DAS-ELISA), Western blot, immune labeling, immunosorbent electron microscopy (ISEM), and/or dot blot).

The procedure to perform a nucleic acid hybridization, an amplification of nucleic acid (e.g., PCR, RT-PCR) or an immunological detection (e.g., precipitation and agglutination tests, ELISA (e.g., Lateral Flow test or DAS-ELISA), Western blot, RIA, immunogold or immunofluorescent labeling, immunosorbent electron microscopy (ISEM), and/or dot blot tests) are performed as described elsewhere herein and well-known by one skilled in the art.

In one embodiment, the evaluating step comprises PCR (semi-quantitative or quantitative), wherein primers are used to amplify one or more nucleic acid sequences of a desirable gene, or a nucleic acid associated with said gene, or QTL or a desirable trait (e.g., a co-segregating nucleic acid, or other marker).

In another embodiment, the evaluating step comprises immunological detection (e.g., precipitation and agglutination tests, ELISA (e.g., Lateral Flow test or DAS-ELISA), Western blot, RIA, immuno labeling (gold, fluorescent, or other detectable marker), immunosorbent electron microscopy (ISEM), and/or dot blot), wherein one or more gene or marker-specific antibodies are used to detect one or more desirable proteins. In one embodiment, said specific antibody is selected from the group consisting of polyclonal antibodies, monoclonal antibodies, antibody fragments, and combination thereof.

Reverse Transcription Polymerase Chain Reaction (RT-PCR) can be utilized in the present disclosure to determine expression of a gene to assist during the selection step of a breeding scheme. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR.

RT-PCR utilizes a pair of primers, which are complementary to a defined sequence on each of the two strands of the mRNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 50° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cation concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using for example agarose gel electrophoresis or other polymer gel like polyacrylamide gels and ethidium bromide (or other nucleic acid staining).

Conventional RT-PCR is a time-consuming technique with important limitations when compared to real time PCR techniques. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general nonspecific DNA Binding Dyes such as SYBR Green I, TaqMan Probes and Molecular Beacons (including Scorpions).

The real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

Other forms of nucleic acid detection can include next generation sequencing methods such as DNA SEQ or RNA SEQ using any known sequencing platform including, but not limited to: Roche 454, Solexa Genome Analyzer, AB SOLiD, Illumina GA/HiSeq, Ion PGM, Mi Seq, among others (Liu et al,. 2012 Journal of Biomedicine and Biotechnology Volume 2012 ID 251364; Franca et al., 2002 Quarterly Reviews of Biophysics 35 pg. 169-200; Mardis 2008 Genomics and Human Genetics vol. 9 pg. 387-402).

In other embodiments, nucleic acids may be detected with other high throughput hybridization technologies including microarrays, gene chips, LNA probes, nanoStrings, and fluorescence polarization detection among others.

In some embodiments, detection of markers can be achieved at an early stage of plant growth by harvesting a small tissue sample (e.g., branch, or leaf disk). This approach is preferable when working with large populations as it allows breeders to weed out undesirable progeny at an early stage and conserve growth space and resources for progeny which show more promise. In some embodiments the detection of markers is automated, such that the detection and storage of marker data is handled by a machine. Recent advances in robotics have also led to full service analysis tools capable of handling nucleic acid/protein marker extractions, detection, storage and analysis.

Quantitative Trait Loci

Breeding schemes of the present application can include crosses between donor and recipient plants. In some embodiments said donor plants contain a gene or genes of interest which may confer the plant with a desirable phenotype. The recipient line can be an elite line having certain favorable traits for commercial production. In one embodiment, the elite line may contain other genes that also impart said line with the desired phenotype. When crossed together, the donor and recipient plant may create a progeny plant with combined desirable loci which may provide quantitatively additive effect of a particular characteristic. In that case, QTL mapping can be involved to facilitate the breeding process.

A QTL (quantitative trait locus) mapping can be applied to determine the parts of the donor plant's genome conferring the desirable phenotype, and facilitate the breeding methods. Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. yield, height, level of resistance to virus, etc.) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait. Knowing the number of QTLs that explains variation in the phenotypic trait tells about the genetic architecture of a trait. It may tell that a trait is controlled by many genes of small effect, or by a few genes of large effect or by a several genes of small effect and few genes of larger effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway- and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping,* 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing one or several genes, i.e. a cluster of genes that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and how do those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, SNPs, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes are generally 50%. Between molecular markers located on the same chromosome the recombination frequency depends on the distance between the markers. A low recombination frequency usually corresponds to a low distance between markers on a chromosome. Comparing all recombination frequencies will result in the most logical order of the molecular markers on the chromosomes. This most logical order can be depicted in a linkage map (Paterson, 1996, Genome Mapping in Plants. R. G. Landes, Austin.). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with a desirable trait in a donor plant can be transferred to a recipient plant to incorporate the desirable trait into progeny plants by transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred to as near isogenic lines (NILs), introgression lines (ILs), backcross inbred lines (BILs), backcross recombinant inbred lines (BCRIL), recombinant chromosome substitution lines (RCSLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the term "pre-ILs" refers to lines which still contain multiple homozygous and/or heterozygous donor segments.

To enhance the rate of progress of introgression breeding, a genetic infrastructure of exotic libraries can be developed. Such an exotic library comprises a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL cover usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, *PLoS Biol.;* 2(10):e245).

Tissue Culture

As it is well known in the art, tissue culture of pepper can be used for the in vitro regeneration of pepper plants. Tissues cultures of various tissues of pepper and regeneration of plants therefrom are well known and published. By way of example, a tissue culture comprising organs has been used to produce regenerated plants as described in Girish-Chandel et al., Advances in Plant Sciences. 2000, 13: 1, 11-17, Costa et al., Plant Cell Report. 2000, 19: 3327-332, Plastira et al., Acta Horticulturae. 1997, 447, 231-234, Zagorska et al., Plant Cell Report. 1998, 17: 12 968-973, Asahura et al., Breeding Science. 1995, 45: 455-459, Chen et al., Breeding Science. 1994, 44: 3, 257-262, Patil et al., Plant and Tissue and Organ Culture. 1994, 36: 2, 255-258. It is clear from the literature that the state of the art is such that these methods of obtaining plants are routinely used and have a very high rate of success. Thus, another aspect of this invention is to provide cells which upon growth and differentiation produce pepper plants having the physiological and morphological characteristics of hybrid pepper plant ALTATA.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. Means for preparing and maintaining plant tissue culture are well known in the art. By way of example, a tissue culture comprising organs has been used to produce regenerated plants. U.S. Pat. Nos. 5,959,185, 5,973, 234, and 5,977,445 describe certain techniques, the disclosures of which are incorporated herein by reference.

EXAMPLES

The foregoing examples of the related art and limitations related therewith are intended to be illustrative and not exclusive. Other limitations of the related art will become apparent to those of skill in the art upon a reading of the specification.

Example 1—Development of New ALTATA Pepper Variety

Breeding History:

Pepper hybrid plant ALTATA has superior characteristics. The female (PEP5847PL) and male (PEP6529PL) parents were crossed to produce hybrid (F1) seeds of ALTATA. The seeds of ALTATA can be grown to produce hybrid plants and parts thereof. The hybrid ALTATA can be propagated by seeds produced from crossing pepper inbred line PEP5847PL with pepper inbred line PE6529PL or vegetatively.

The origin and breeding history of hybrid plant ALTATA can be summarized as follows: the line PEP5847PL (a proprietary line owned by HM.CLAUSE, S.A.) was used as the female plant and crossed by pollen from PE6529PL (a proprietary line owned by HM.CLAUSE, S.A.).

The first trial planting of this hybrid was done during the fall in Los Mochis (Mexico). Additional testing was done in Culiacan (Mexico). This hybrid was further trialed for three years, an example of such trial being disclosed in tables 2 to 5.

The inbred line PEP5847PL is used as the female parent in this cross. PEP5847PL can be characterized as a tall plant with a medium to heavy cover and with a good set of large size fruit. The fruit shape is slightly more elongated than wide with very squared uniform shape. The fruit mature from green to red.

The inbred line PE6529PL is used as the male parent in this cross. PE6529PL can be characterized as a medium plant with a good cover, and a spread set of large and extra-large size fruit. The fruit is as elongated as wide with a very square, uniform shape. The fruit mature from green to lemon yellow.

Pepper hybrid plant ALTATA is similar to pepper hybrid plant RINSKA. RINSKA is a commercial variety. While similar to pepper hybrid plant RINSKA, there are significant differences including fruit ratio length/diameter is large in ALTATA while it is medium in RINSKA; Fruit shape in longitudinal section is rectangular in ALTATA while RINSKA is square; time of maturity is late in ALTATA while RINSKA is early; depth of interloculary grooves is absent or very shallow in ALTATA while RINSKA is medium; the time to maturity is medium in ALTATA while it is early in RINSKA; the resistance to disease is also different, L4 gene conferring resistance to the Pepper Mild Mottle Virus (1-2-3) [PMMoV123] is present in ALTATA while it is absent in RINSKA; resistance to Tomato Spotted Wilt Virus, wild type [TSWV:wt] is present in ALTATA while it is absent in RINSKA.

Some of the criteria used to select the hybrid ALTATA as well as their inbred parent lines in various generations include: high yield, uniform fruit set, fruit size and color, uniform fruit size and shape, and a high tolerance to cracking.

The pepper hybrid plant ALTATA has shown uniformity and stability for the traits, within the limits of environmental influence for the traits as described in the following Variety Descriptive Information. No variant traits have been observed or are expected for agronomical important traits in pepper hybrid ALTATA.

Pepper hybrid plant ALTATA has the following morphologic and other characteristics, as compared to RINSKA (based primarily on data collected in Culiacan, Sin., Mexico and Los Mochis, Sin., Mexico, all experiments done under the direct supervision of the applicant).

TABLE 1

Characteristics of ALTATA in comparison to RINSKA based on UPOV's test guidelines for Distinctness, Uniformity and Stability
Genus: *Capsicum*
Species: *Capsicum annuum*

| Plant type: Sweet Pepper | ALTATA | RINSKA |
|---|---|---|
| | Rating | Rating |
| Seedling: anthocyanin coloration of hypocotyl | absent | absent |
| Plant: habit (Attitude) | upright | upright |
| Plant: length of stem (from cotyledon to first flower) | medium | short |
| Plant: shortened internode (in upper part) | absent | absent |
| Varieties without shortened | medium | medium |

TABLE 1-continued

Characteristics of ALTATA in comparison to RINSKA based on UPOV's test guidelines for Distinctness, Uniformity and Stability
Genus: *Capsicum*
Species: *Capsicum annuum*

| Plant type: Sweet Pepper | ALTATA | RINSKA |
|---|---|---|
| internodes only: Plant: length of internode (on primary side shoots) | | |
| Plant: anthocyanin coloration of nodes | absent | absent |
| Plant: intensity of anthocyanin coloration of stem nodes | N/A | N/A |
| Plant: hairiness of stem nodes | absent or very weak | absent or very weak |
| Plant: height | tall | tall |
| Plant: leaf cover | medium to heavy | medium to heavy |
| Leaf: length of blade | long | long |
| Leaf: width of blade | broad | medium |
| Leaf: petiole length (cm) | 10.8 | 10.5 |
| Leaf: intensity of green color | dark | dark |
| Leaf: shape | broad elliptic | broad elliptic |
| Leaf: undulation of margin | absent or very weak | medium |
| Leaf: blistering | very weak | very weak |
| Leaf: profile in cross section | moderately concave | moderately concave |
| Leaf: glossiness | weak | very weak |
| Flower: anthocyanin coloration in anther | present | present |
| Fruit: type | Bell | Bell |
| Fruit: color (before maturity) | green | green |
| Fruit: intensity of color (before maturity) | medium | dark |
| Fruit: anthocyanin coloration | absent | absent |
| Fruit: attitude | drooping | drooping |
| Fruit: peduncle attitude | drooping | drooping |
| Fruit: length | long | short |
| Fruit: diameter | broad | medium |
| Fruit: ratio length/diameter | large | medium |
| Fruit: shape in longitudinal section | rectangular | square |
| Fruit: shape in cross section (at level of placenta) | angular | angular |
| Fruit: sinuation of pericarp at basal part | absent or very weak | strong |
| Fruit: sinuation of pericarp excluding basal part | absent or very weak | absent or very weak |
| Fruit: texture of surface | smooth or very slightly wrinkled | smooth or very slightly wrinkled |
| Fruit: color | red | red |
| Fruit: intensity of color (at maturity) | medium | medium |
| Fruit: glossiness | strong | strong |
| Fruit: stalk cavity | present | present |
| Fruit: depth of stalk cavity | very shallow | very shallow |
| Fruit: shape of apex | moderately depressed | rounded |
| Fruit: depth of interloculary grooves | absent or very shallow | medium |
| Fruit: number of locules | equally three and four | equally three and four |
| Fruit: thickness of flesh | thick | thick |
| Fruit: stalk length | very short | very short |
| Fruit: stalk thickness | medium | medium |
| Fruit: calyx aspect | non-enveloping | non-enveloping |
| Fruit: capsaicin in placenta | absent | absent |
| Fruit: flavor | strong pepper flavor extended | strong pepper flavor extended |
| Fruit: setting pattern | 1 | 1 |
| Flower: flower number per leave axil | | |
| Flower: number calyx lobes | 7 | 7 |
| Flower: number petals | 7 | 5 |
| Flower: corolla color | white | white |
| Flower: corolla throat markings | white | white |
| Flower: style length | less than stamen | equal to stamen |
| Flower: self-incompatibility | absent | absent |
| Seed: color | cream | cream |
| Anthocyanin: stem | absent | absent |
| Anthocyanin: node | absent | absent |
| Anthocyanin: leaf | absent | absent |
| Anthocyanin: pedicel | absent | absent |
| Anthocyanin: calyx | absent | absent |
| Time of beginning of flowering (first flower on second flowering node) | early | early |
| Time of maturity | medium | early |
| Resistance to Tobamovirus | | |
| Pathotype 0 (Tobacco Mosaic Virus (0)) | present | present |
| Pathotype 1-2 (Tomato Mosaic Virus (1-2)) | present | present |
| Pathotype 1-2-3 (Pepper Mild Mottle Virus (1-2-3)) | present | absent |
| Resistance to Potato Virus Y (PVY) | | |
| Pathotype 0 | absent | absent |
| Pathotype 1 | absent | absent |
| Pathotype 1-2 | absent | absent |
| Resistance to Phytophthora capsici | absent | absent |
| Resistance to Cucumber Mosaic Virus (CMV) | absent | absent |
| Resistance to Tomato Spotted Wilt Virus (TSWV) | present | absent |
| Resistance to *Xanthomonas campestris* pv. *vesicatoria* | | |
| Xcv 0, 1, 2, 3 7, 8 | present | absent |
| Xcv 0, 1, 2, 3, 4, 5, 7, 8, 9 | absent | absent |
| Xcv 0, 1, 2, 3, 4, 5, 6, 7, 8, 9, 10 | absent | absent |
| bs5 gene | absent | absent |

Example 2—Field Trials Characteristics of Hybrid Pepper Plant ALTATA

In Tables 2, 3, 4 and 5 the traits and characteristics of hybrid pepper plant ALTATA are compared to the variety RINSKA. The data was collected during one growing season from several field locations in Mexico, all experiments done under the direct supervision of the applicant.

In Table 2 and 3, the first line shows the trial location, the second line shows the "transplanting date", the third lines shows the "1$^{st}$ harvest date", the fourth line shows the "2$^{nd}$ harvest date", the fifth line shows the "3$^{rd}$ harvest date", the sixth line shows the "4th harvest date", the seventh line shows the "5$^{th}$ harvest date", the eighth line shows the "Variety name", the tenth through fifteenth lines show the "Yield" in the kilograms per square meter (kg·m$^{-2}$)". Line tenth shows the yield of "Jumbo fruit" which are those fruit greater than 4 inches in diameter. Line eleven shows the yield of "Extra-large fruit" which are those fruit greater than 3.5 inches in diameter and less than 4 inches in diameter. Line twelve shows the yield of "Large fruit" which are those greater than 3 inches in diameter and less than 3.5 inches in diameter. Line thirteen shows the yield of "Medium fruit" which are those greater than 2 inches in diameter and less than 2.75 inches in diameter. Line fourteen shows the "Total Yield" of all fruit sizes.

TABLE 2

| Trial location | Culiacan, Mexico | |
|---|---|---|
| Transplanting date | 8-September | |
| 1st harvest date | 22-December | |
| 2nd harvest date | 19-January | |
| 3rd harvest date | 23-February | |
| 4th harvest date | 23-March | |
| 5th harvest date | 20-April | |
| | Variety name | |
| | ALTATA | RINSKA |
| | Yield (kg · m$^{-2}$) | |
| Jumbo fruit | 0.59 | 0.0 |
| Extra-large fruit | 2.17 | 0.69 |
| Large fruit | 0.99 | 3.4 |
| Medium fruit | 0.19 | 0.84 |
| Total Yield | 3.94 | 4.93 |

TABLE 3

| Trial location | Los Mochis, Mexico | |
|---|---|---|
| Transplanting date | 14-September | |
| 1st harvest date | 7-December | |
| 2nd harvest date | 4-January | |
| 3rd harvest date | 8-February | |
| 4th harvest date | 8-March | |
| 5th harvest date | 5-April | |
| | Variety name | |
| | ALTATA | RINSKA |
| | Yield (kg · m$^{-2}$) | |
| Jumbo fruit | 2.64 | 0.13 |
| Extra-large fruit | 1.32 | 1.25 |
| Large fruit | 2.47 | 1.84 |
| Medium fruit | 1.81 | 3.36 |
| Total Yield | 8.24 | 6.52 |

In table 4 and 5 the first line shows the "Trial location", the second line shows the "Transplanting date", the third line shows the "Evaluation date" and the fourth line shows the "Variety name". The sixth line "Height of the plant" rates the plant height on a 1 to 9 scale with 1=very short, 2=very short to short, 3=short, 4=short to medium, 5=medium, 6=medium to tall, 7=tall, 8=tall to very tall, 9=very tall, the seventh line "Cover of the plant" rates the plant cover on a 1 to 9 scales with 1=very poorly covered, 2=very poorly to poorly covered, 3=poorly covered, 4=poorly covered to medium coverage, 5=medium coverage, 6=medium coverage to well covered, 7=well covered, 8=well covered to very covered, 9=very covered. Line eight, "Type of fruits in the box", rates the fruit on a 1 to 9 scale with 1=very short, 2=very short to short, 3=short, 4=short to medium, 5=medium, 6=medium to elongated, 7=elongated, 8=elongated to very elongated, 9=very elongated, line nine "Mature color of fruits in the box" rates the fruit color on a X.Y scale with X, mature color of the fruit on a 1 to 3 scale, with 1=yellow, 2=orange, 3=red and Y, intensity of the mature color on a 1 to 9 scale, with 1=very light, 2=very light to light, 3=light, 4=light to medium, 5=medium, 6=medium to dark, 7=dark, 8=dark to very dark, 9=very dark. Line ten rates the "Size of fruits in the box" on a 1 to 9 scale with 1=small, 2=small to medium, 3=medium, 4=medium to large, 5=large, 6=large to extra-large, 7=extra-large, 8=extra-large to jumbo, 9=jumbo, line eleven rates the fruit "Production in the box" per plot on a 0 to 9 scale with 0=no fruit, 1=box 12.5% full, 2=box 25% full, 3=box 37.5% full, 4=box 50% full, 5=box 62.5% full, 6=box 75% full, 7=box 87.5% full, 8=box 100% full.

TABLE 4

| Trial Location | Culiacan, Mexico | |
|---|---|---|
| Transplanting Date | 8-September | |
| Evaluation Date | 23-February | |
| | Variety Name | |
| | ALTATA | RINSKA |
| Trait Type | Trait value | |
| Height of the plant | 6 | 6 |
| Cover of the plant | 6 | 7 |
| Type of fruits in the box | 5 | 4 |
| Mature color of fruits in the box | 3.6 | 3.6 |
| Size of fruits in the box | 8 | 7 |
| Production in the box | 4 | 5 |

TABLE 5

| Trial Location | Los Mochis, Mexico | |
|---|---|---|
| Transplanting Date | 14-September | |
| Evaluation Date | 4-January | |
| | Variety Name | |
| | ALTATA | RINSKA |
| Trait type | Trait value | |
| Height of the plant | 5 | 6 |
| Cover of the plant | 8 | 7 |
| Type of fruits in the box | 5 | 4 |
| Mature color of fruits in the box | 3.6 | 3.6 |
| Size of fruits in the box | 8 | 7 |
| Production in the box | 6 | 5 |

Deposit Information

A deposit of the pepper seed of this invention is maintained by HM.CLAUSE, Inc., 5820 Research Way, Immokalee, Florida 34142, USA. In addition, a sample of the hybrid pepper seed of this invention has been deposited with the National Collections of Industrial, Food and Marine Bacteria (NCIMB), 23 St Machar Drive, Aberdeen, Scotland, AB24 3RY, United Kingdom.

To satisfy the enablement requirements of 35 U.S.C. 112, and to certify that the deposit of the isolated strain of the present invention meets the criteria set forth in 37 CFR 1.801-1.809, Applicants hereby make the following statements regarding the deposited hybrid pepper ALTATA (deposited as NCIMB Accession No. 44199 on Aug. 3, 2023).

1. During the pendency of this application, access to the invention will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and 5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same variety with the NCIMB.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A seed of hybrid pepper designated ALTATA, wherein a representative sample of seeds of said hybrid has been deposited under NCIMB No. 44199.

2. A pepper plant, a plant part thereof, or a plant cell thereof, produced by growing the seed of claim 1, wherein the pepper plant and a pepper plant produced from the plant part or the plant cell have has-all of the physiological and morphological characteristics of hybrid ALTATA when grown under the same environmental conditions.

3. The pepper plant part, or the plant cell thereof of claim 2, wherein the pepper part is selected from the group consisting of a leaf, a flower, a fruit, a stalk, a cell, a root, a rootstock, a meristem, and a scion.

4. A tissue culture of regenerable cells produced from the pepper plant or plant part of claim 2.

5. A pepper plant regenerated from the tissue culture of claim 4, wherein the pepper plant has all of the physiological and morphological characteristics of hybrid ALTATA when grown under the same environmental conditions.

6. A method for harvesting a pepper fruit, the method comprising (a) growing the pepper plant of claim 2 to produce a pepper fruit, and (b) harvesting said pepper fruit.

7. A method for producing a pepper seed, the method comprising crossing a first parent pepper plant with a second parent pepper plant and harvesting the resultant pepper seed, wherein said first parent pepper plant and/or second parent pepper plant is the pepper plant of claim 2.

8. A method for producing a pepper seed, the method comprising self-pollinating the pepper plant of claim 2 and harvesting the resultant pepper seed.

9. A method of vegetatively propagating the pepper plant of claim 2, said method comprising (a) collecting part of the plant of claim 2 and (b) regenerating a plant from said part.

10. The method of claim 9, further comprising harvesting a fruit from said plant.

11. A plant obtained from the method of claim 9, wherein said plant has all of the physiological and morphological characteristics of hybrid ALTATA when grown under the same environmental conditions.

12. A pepper fruit selected from the group consisting of: (a) a pepper fruit produced from the plant of claim 2; (b) a pepper fruit produced by the method of claim 6; and (c) a pepper fruit produced from the method of claim 10, wherein the pepper fruit has all of the physiological and morphological characteristics of a fruit of pepper hybrid ALTATA when grown under the same environmental conditions.

13. A method of producing a pepper plant derived from the hybrid pepper plant ALTATA, the method comprising:
(a) self-pollinating the pepper plant of claim 2 at least once to produce a progeny pepper plant derived from the hybrid pepper variety ALTATA.

14. The method of claim 13, further comprising the steps of:
(b) crossing the progeny pepper plant derived from the hybrid pepper plant ALTATA with itself or a second pepper plant to produce a progeny seed of a subsequent generation;
(c) growing a progeny plant from the progeny seed of the subsequent generation;
(d) crossing the progeny plant of the subsequent generation with itself or a second pepper plant to produce a pepper plant derived from the hybrid pepper plant ALTATA; and
(e) repeating step (b) and (c) for at least one generation to produce a pepper plant further derived from the pepper hybrid ALTATA.

15. A method of producing a pepper plant derived from the hybrid pepper plant ALTATA, the method comprising;
(a) crossing the pepper plant of claim 2 with a second pepper plant to produce a progeny pepper plant derived from the hybrid pepper variety ALTATA.

16. The method of claim 15, further comprising the steps of:
(b) crossing the progeny pepper plant derived from the hybrid pepper plant ALTATA with itself or a second pepper plant to produce a progeny seed of a subsequent generation;
(c) growing a progeny plant from the progeny seed of the subsequent generation;
(d) crossing the progeny plant of the subsequent generation with itself or a second pepper plant to produce a pepper plant derived from the pepper hybrid pepper plant ALTATA; and
(e) repeating step (b) and (c) to produce a pepper plant further derived from the hybrid pepper plant ALTATA.

17. A method of producing a plant of hybrid pepper designated ALTATA comprising at least one desired trait, the method comprising introducing a single locus conversion conferring the desired trait into hybrid pepper designated ALTATA whereby a plant of hybrid pepper designated ALTATA comprising the desired trait is produced, wherein a representative sample of seeds of said hybrid pepper designated ALTATA has been deposited under NCIMB No. 44199.

18. A pepper plant, wherein said pepper plant comprises a single locus conversion and otherwise all of the physiological and morphological characteristics of hybrid pepper plant ALTATA, and wherein a representative sample of seeds of hybrid pepper designated ALTATA has been deposited under NCIMB No. 44199.

19. The plant of claim 18, wherein the single locus conversion confers said plant with herbicide resistance, male sterility, male fertility, insect resistance, disease resistance, water stress tolerance, heat tolerance, improved standability, enhanced plant vigor, improved shelf life, delayed senescence or controlled ripening, and increased nutritional quality compared to a plant not comprising said single locus conversion.

20. The plant of claim 18, wherein the single locus conversion is an artificially mutated gene or an artificially mutated nucleotide sequence.

21. The plant of claim 18, wherein the single locus conversion is a gene that has been modified through a genome editing technique with a nuclease selected from the group consisting of Zinc finger nuclease (ZFN), Transcription Activation-Like Effector Nuclease (TALEN), Clustered Regularly Interspaced Short Palindromic Repeats-associated Cas endonuclease (CRISPR-Cas), meganuclease, homing endonuclease, and RNA-guided endonuclease.

22. A method of producing a pepper plant, the method comprising grafting a rootstock or a scion of the hybrid pepper plant of claim 2 to another pepper plant.

23. A method for producing nucleic acids, the method comprising isolating nucleic acids from the plant of claim 2, a plant part, or a plant cell thereof.

24. A method for producing a second pepper plant, the method comprising applying plant breeding techniques to the plant or plant part of claim 2 to produce the second pepper plant.

25. A method of producing a commodity plant product, the method comprising obtaining the plant of claim 2 or a part thereof and producing said commodity plant product therefrom.

* * * * *

UNITED STATES PATENT AND TRADEMARK OFFICE
CERTIFICATE OF CORRECTION

PATENT NO. : 12,302,852 B2  
APPLICATION NO. : 17/871704  
DATED : May 20, 2025  
INVENTOR(S) : Bruno Bouffier Page 1 of 1

It is certified that error appears in the above-identified patent and that said Letters Patent is hereby corrected as shown below:

In the Claims

In Claim 2, at Column 43, Line 31:
DELETE: "has-"

Signed and Sealed this
First Day of July, 2025

Coke Morgan Stewart
*Acting Director of the United States Patent and Trademark Office*